(12) United States Patent
Arnett et al.

(10) Patent No.: US 11,684,766 B2
(45) Date of Patent: Jun. 27, 2023

(54) COUPLING MECHANISM FOR MEDICAL DEVICES

(71) Applicant: BOSTON SCIENTIFIC MEDICAL DEVICE LIMITED, Galway (IE)

(72) Inventors: Jeffery Arnett, Gilbert, AZ (US); Linus Leung, Toronto (CA); Moussa Chehade, Toronto (CA); John Paul Urbanski, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 316 days.

(21) Appl. No.: 16/682,825

(22) Filed: Nov. 13, 2019

(65) Prior Publication Data
US 2020/0147360 A1 May 14, 2020

Related U.S. Application Data

(63) Continuation-in-part of application No. PCT/IB2019/053755, filed on May 8, 2019.
(Continued)

(51) Int. Cl.
*A61M 39/10* (2006.01)
*A61M 25/06* (2006.01)
*A61M 39/02* (2006.01)

(52) U.S. Cl.
CPC ........ *A61M 39/10* (2013.01); *A61M 25/0662* (2013.01); *A61M 39/1011* (2013.01);
(Continued)

(58) Field of Classification Search
CPC .......... A61M 25/0097; A61M 25/0606; A61M 25/0662; A61M 2025/0004;
(Continued)

(56) References Cited

U.S. PATENT DOCUMENTS 3,990,727 A * 11/1976 Gallagher ............. F16L 37/084
285/26
4,844,512 A * 7/1989 Gahwiler ................ F16L 37/53
285/39
(Continued)

FOREIGN PATENT DOCUMENTS

CN 204601342 U 9/2015
EP 1144041 A2 10/2001
(Continued)

OTHER PUBLICATIONS

International Search Report and Written Opinion received for PCT Patent Application No. PCT/IB2019/053755, dated Sep. 16, 2019, 13 pages.

*Primary Examiner* — Kami A Bosworth
(74) *Attorney, Agent, or Firm* — Nelson Mullins Riley & Scarborough LLP

(57) ABSTRACT

A releasable coupling mechanism for coupling a delivery catheter and a dilator. The delivery catheter comprising a delivery catheter hub at the proximal end and the dilator comprising a dilator hub at the proximal end. The proximal end of the delivery catheter hub comprises a coupling member for releasably receiving a raised portion which is positioned at a distal end of the dilator hub. The coupling member has a pair of engagement members positioned on opposing sides of the coupling member and configured to releasably engage the raised portion. The delivery catheter hub further comprising at least one indicia on the housing. The indicia indicate an orientation of the delivery catheter hub such that the dilator hub disengages from the coupling member by simultaneously deflecting the pair of engagement members.

15 Claims, 28 Drawing Sheets

Related U.S. Application Data

(60) Provisional application No. 62/668,700, filed on May 8, 2018.

(52) U.S. Cl.
CPC .............. *A61M 2025/0681* (2013.01); *A61M 2025/0687* (2013.01); *A61M 2039/0229* (2013.01); *A61M 2039/1016* (2013.01); *A61M 2039/1061* (2013.01)

(58) Field of Classification Search
CPC .. A61M 2025/0006; A61M 2025/0008; A61M 2025/0681; A61M 29/00; A61M 39/10; A61M 39/1011; A61M 39/1016; A61M 39/1027; A61M 39/1044; A61M 39/1061; A61M 2039/0229; A61B 17/34; A61B 17/3415; A61B 17/3421; A61B 2017/00477; A61B 2017/347
See application file for complete search history.

(56) References Cited

U.S. PATENT DOCUMENTS

| | | | | |
|---|---|---|---|---|
| 5,090,747 A | | 2/1992 | Kotake | |
| 5,213,376 A | * | 5/1993 | Szabo | F16L 37/084 285/39 |
| 5,324,080 A | * | 6/1994 | McNaughton | F16L 37/084 285/39 |
| 5,356,183 A | * | 10/1994 | Cole | F16L 25/0045 285/148.27 |
| 5,374,088 A | * | 12/1994 | Moretti | F16L 37/0985 285/305 |
| 5,466,017 A | * | 11/1995 | Szabo | F16L 37/0987 285/319 |
| 5,520,420 A | * | 5/1996 | Moretti | F16L 37/00 285/81 |
| 5,573,279 A | | 11/1996 | Rea et al. | |
| 7,217,256 B2 | | 5/2007 | Di Palma | |
| 7,240,926 B2 | * | 7/2007 | Dalle | A61M 39/1011 285/308 |
| 8,192,401 B2 | | 6/2012 | Morris et al. | |
| 9,636,278 B2 | * | 5/2017 | Sanders | A61J 1/2058 |
| 9,700,701 B2 | | 7/2017 | Benjamin et al. | |
| 2002/0149200 A1 | * | 10/2002 | Fumioka | F16L 37/23 285/81 |
| 2006/0058579 A1 | * | 3/2006 | Oberlaender | A61B 17/3462 600/102 |
| 2006/0264911 A1 | | 11/2006 | Nelson | |
| 2006/0267341 A1 | | 11/2006 | Takayanagi | |
| 2007/0021648 A1 | * | 1/2007 | Lenker | A61M 25/0097 600/29 |
| 2011/0251597 A1 | * | 10/2011 | Bharadwaj | A61B 17/1757 606/1 |
| 2016/0271364 A1 | | 9/2016 | Rowe et al. | |
| 2017/0009920 A1 | * | 1/2017 | Canatella | F16L 37/0985 |

FOREIGN PATENT DOCUMENTS

| | | |
|---|---|---|
| JP | 2010137043 A | 6/2010 |
| WO | 0015287 A2 | 3/2000 |
| WO | 2006130378 A1 | 12/2006 |
| WO | 2011049824 A1 | 4/2011 |
| WO | 2016018998 A1 | 2/2016 |

\* cited by examiner

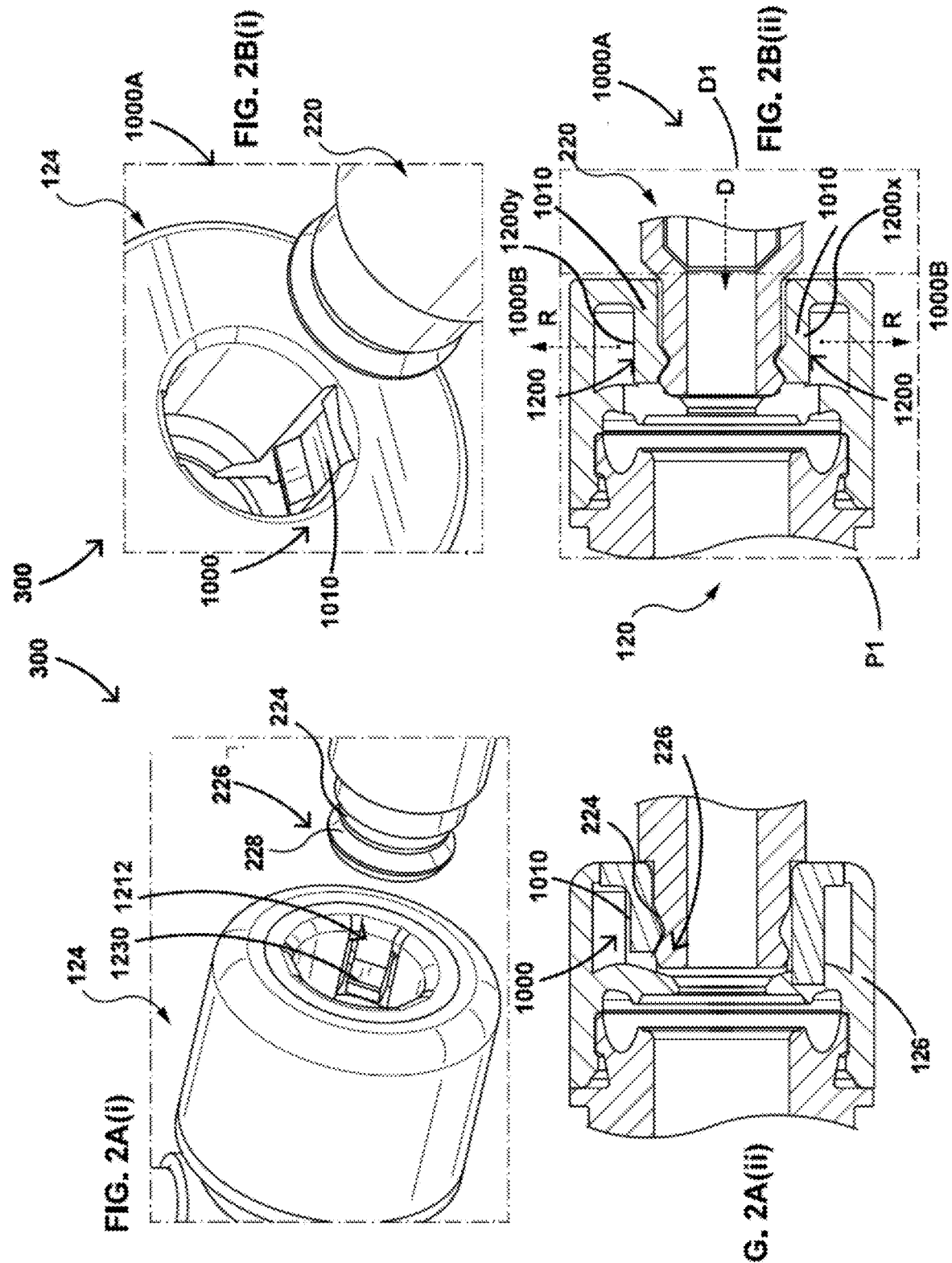

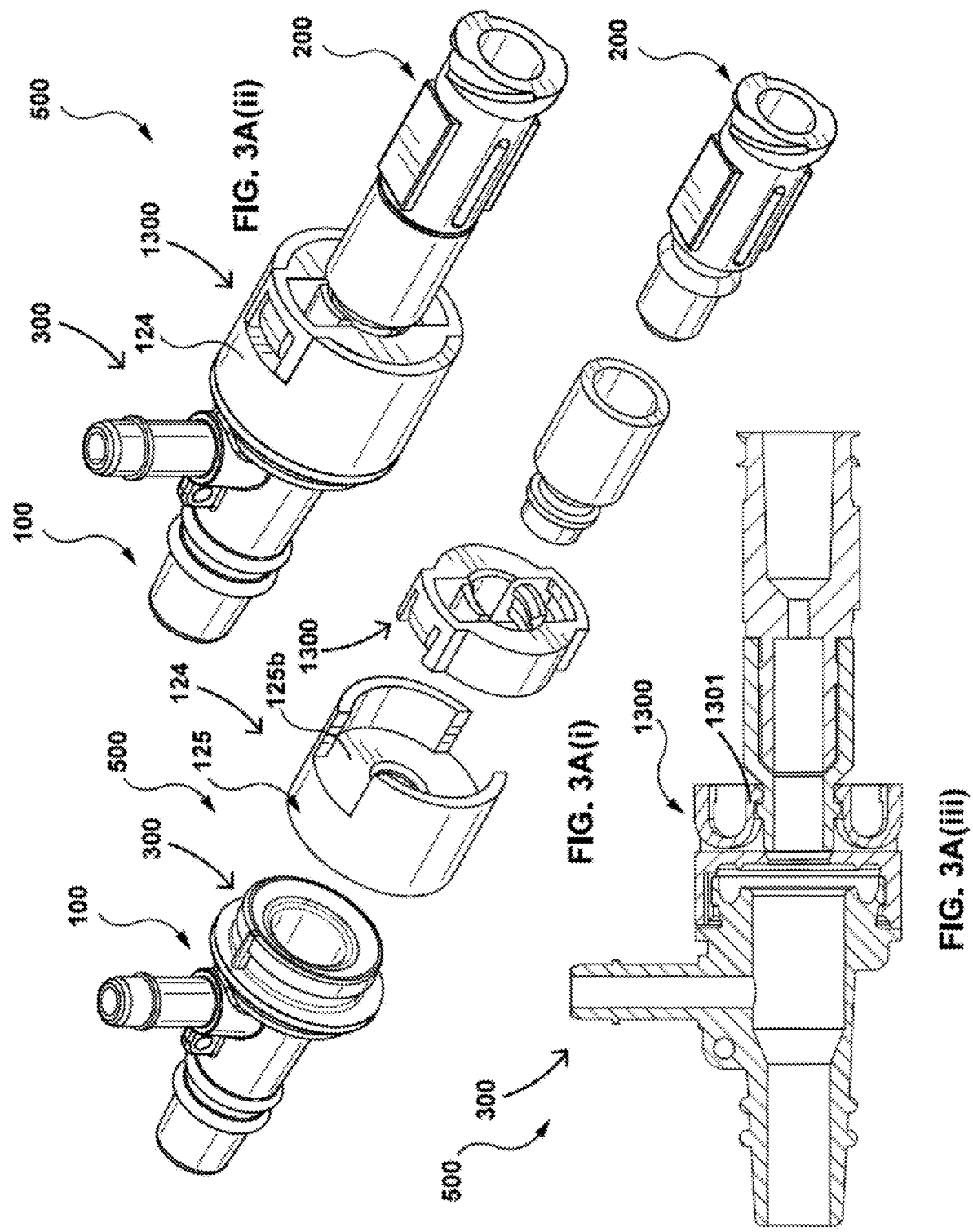

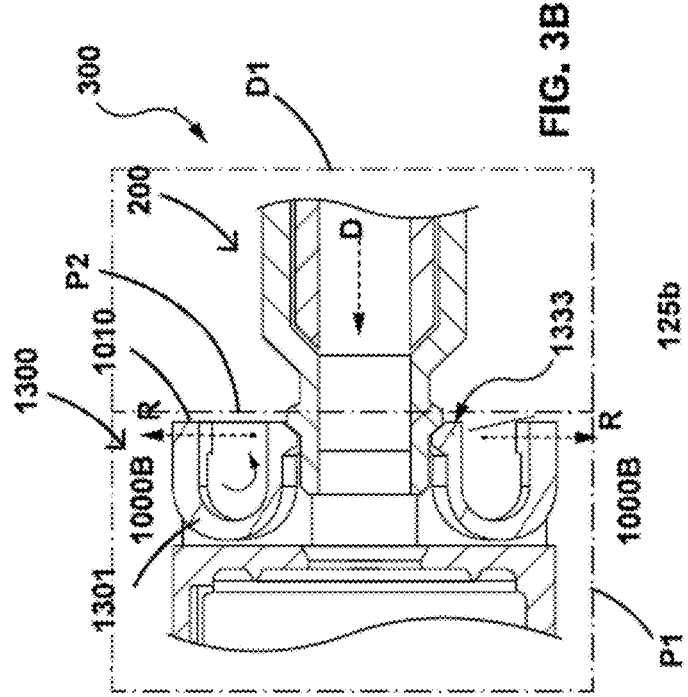
FIG. 3B
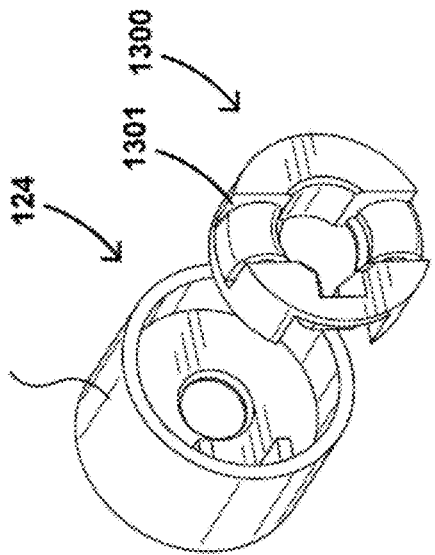
FIG. 3D(ii)
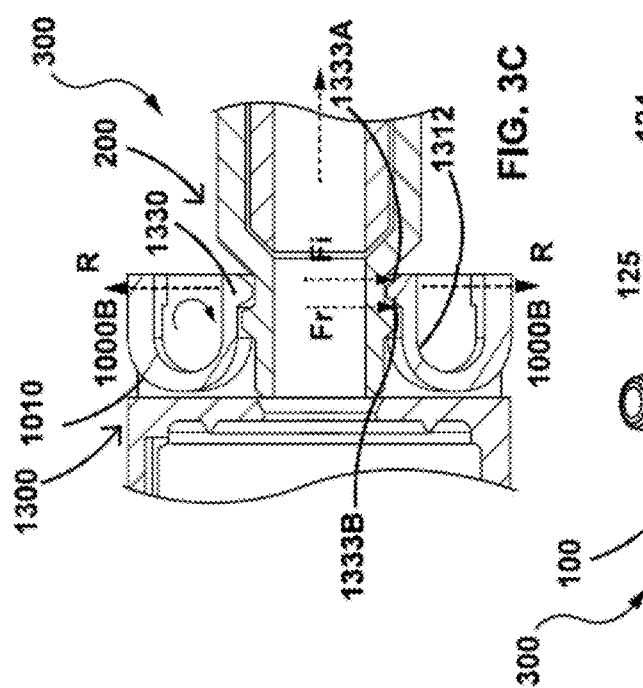
FIG. 3C
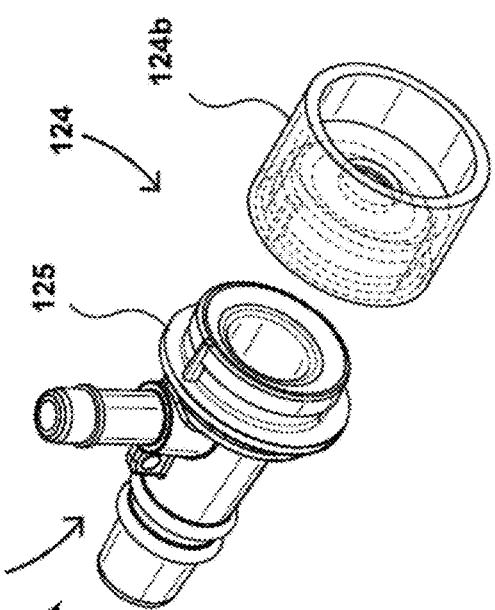
FIG. 3D(i)

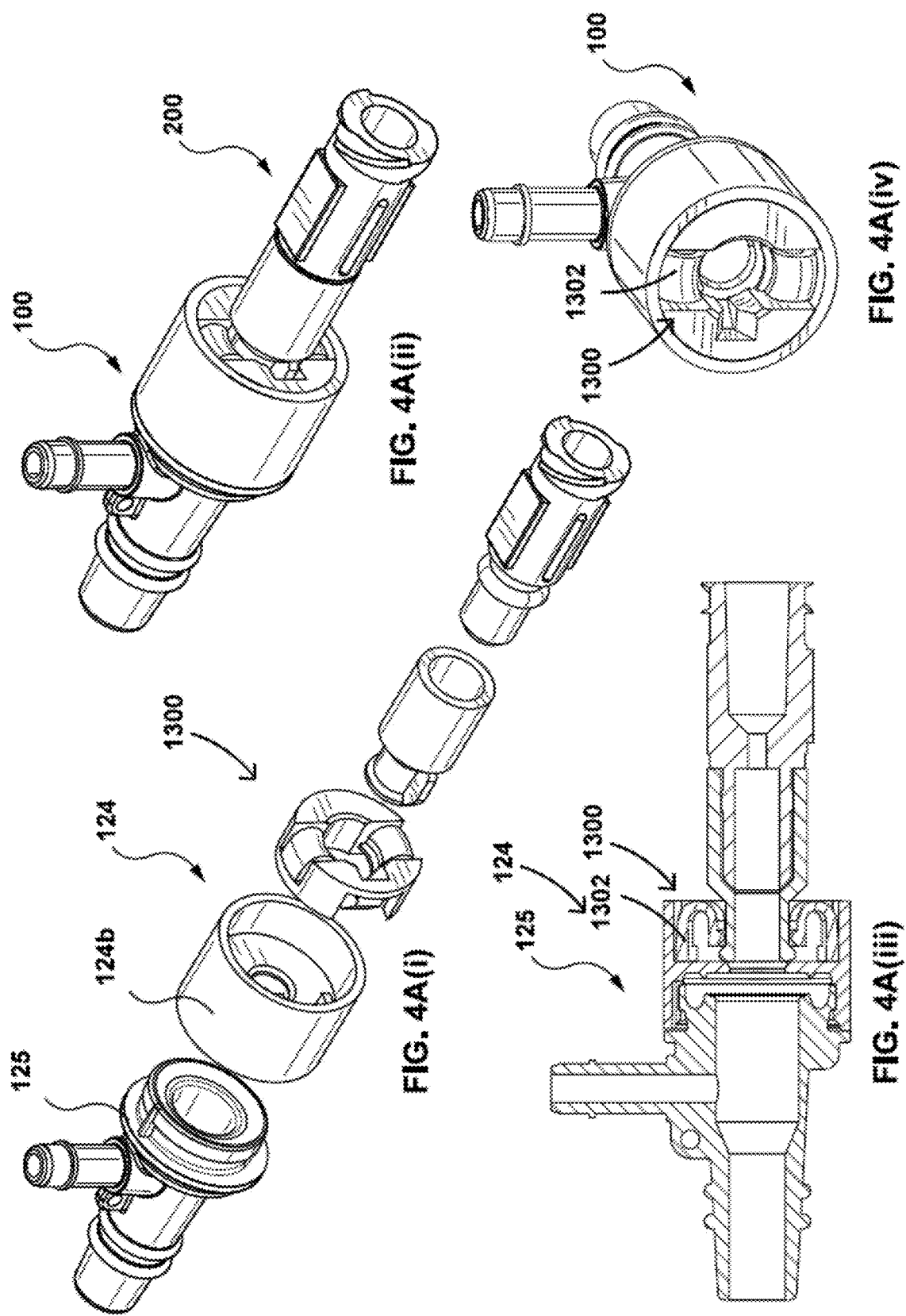

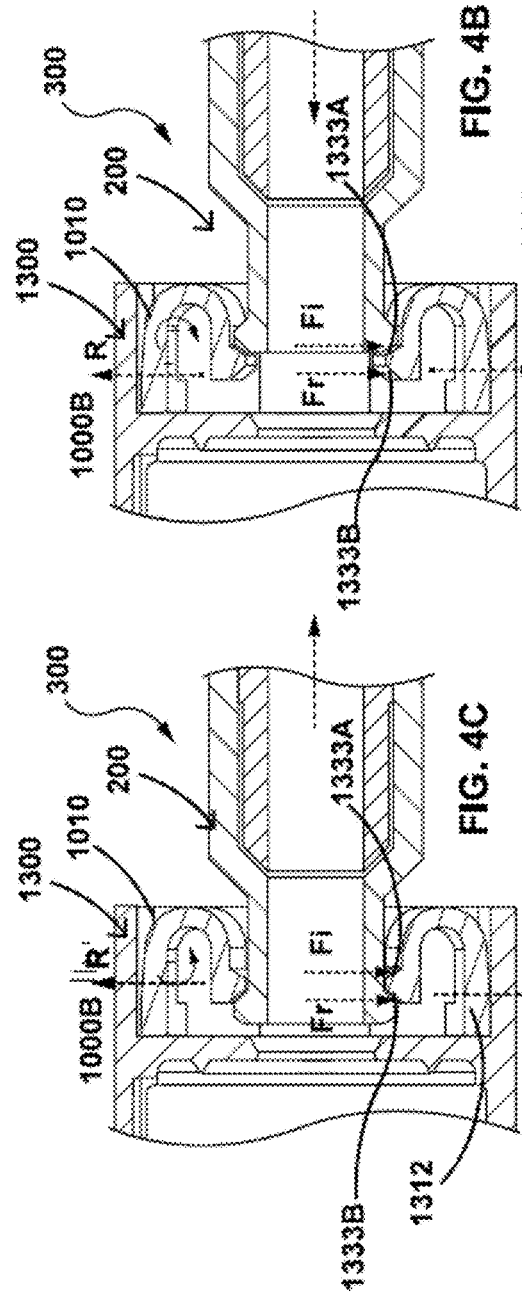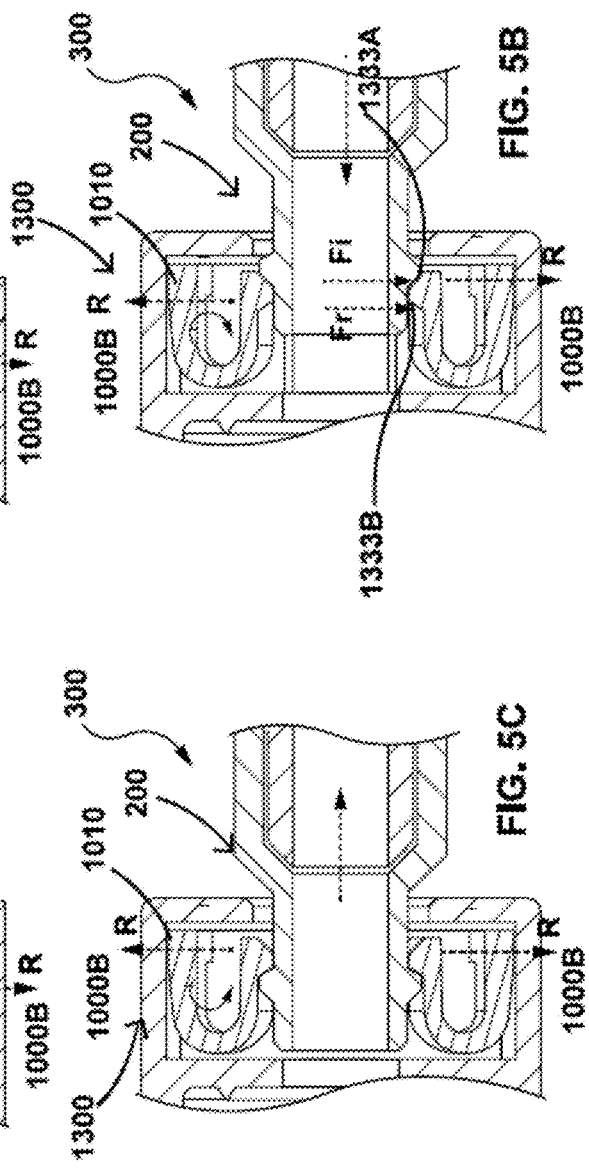

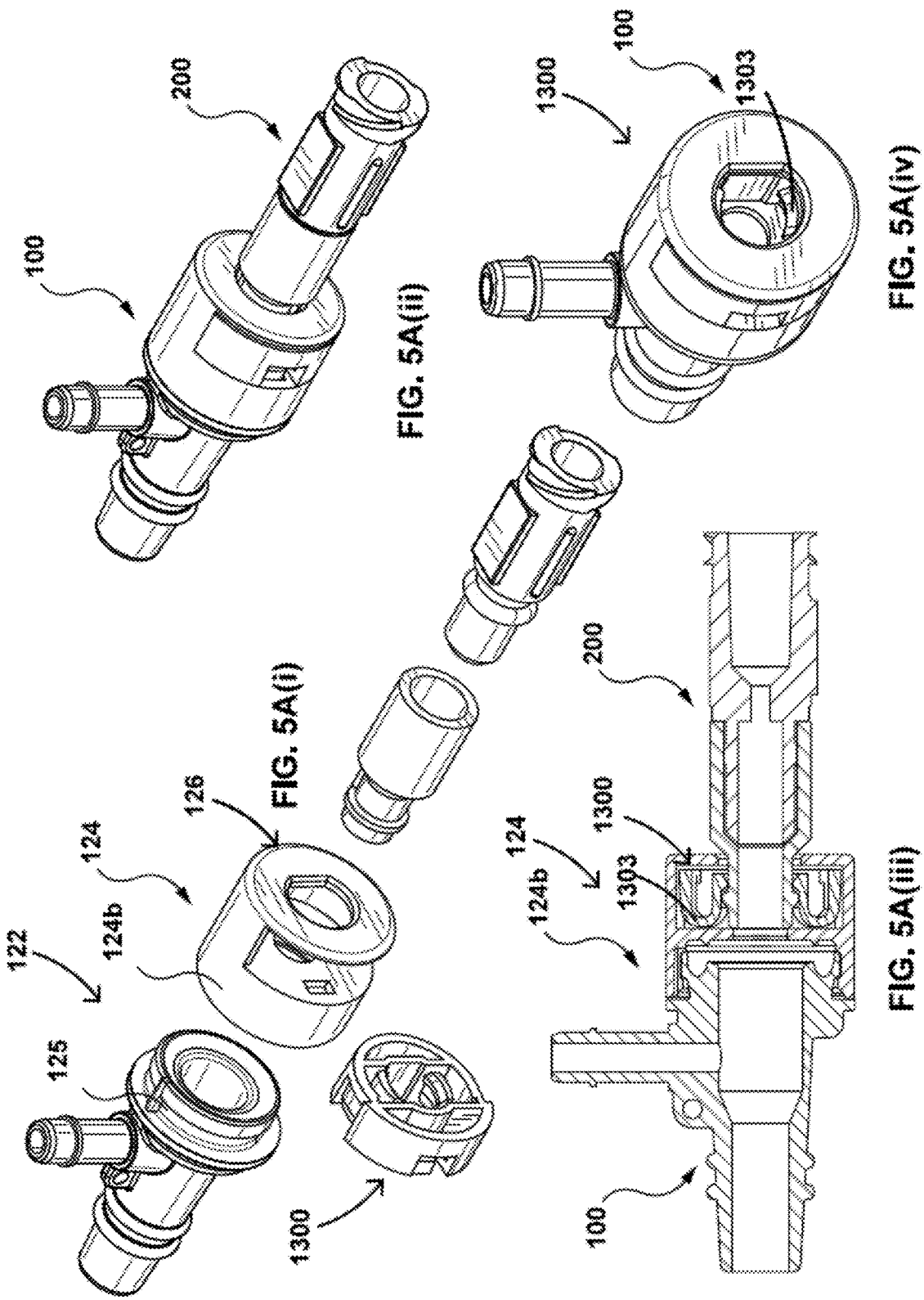

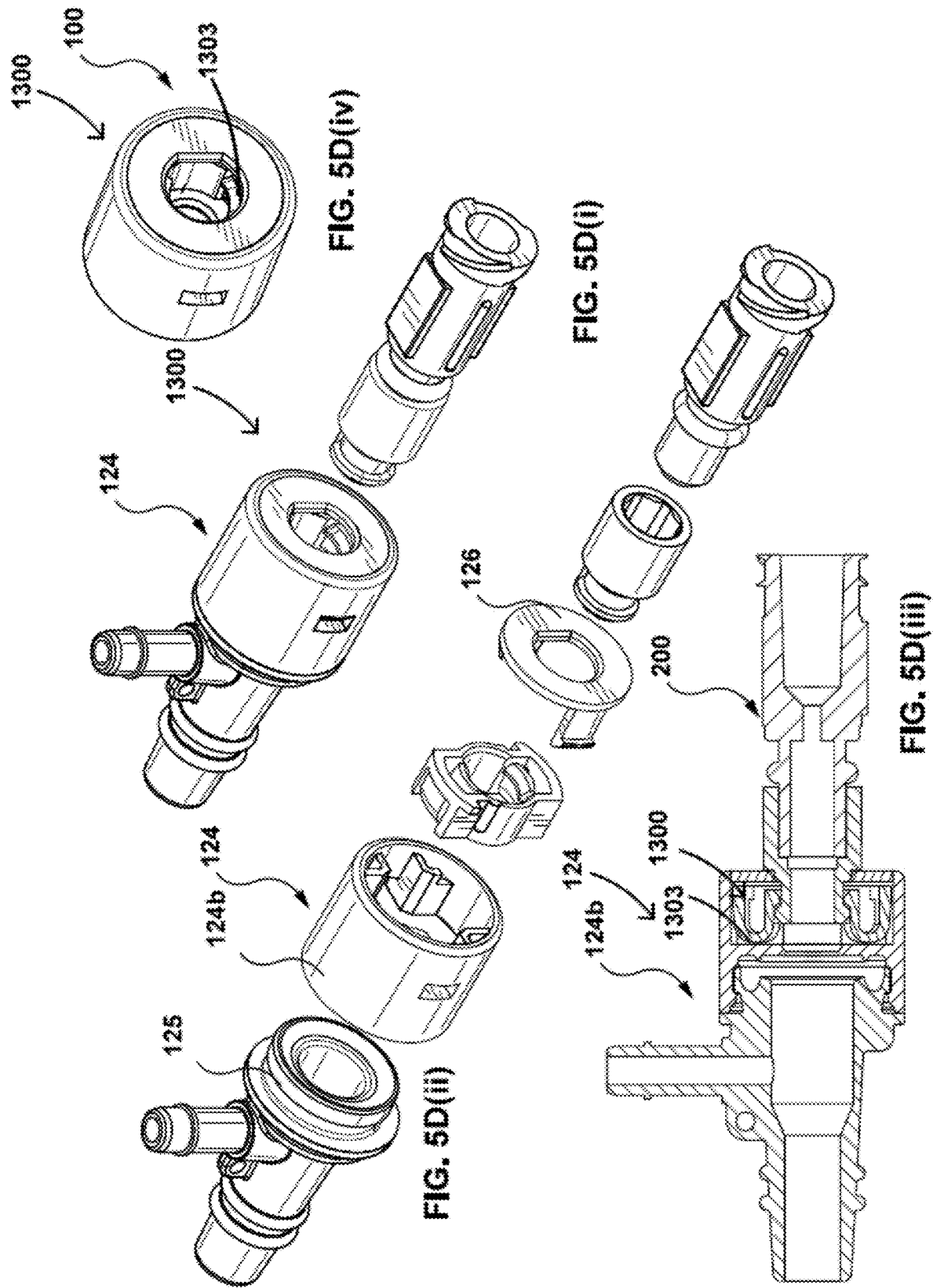

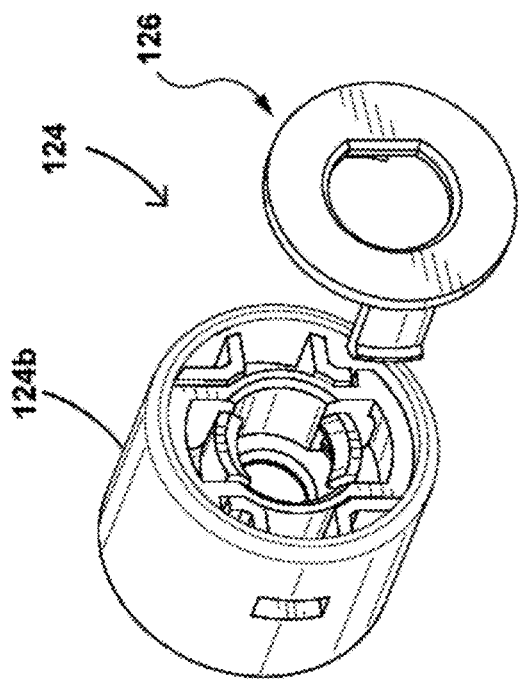
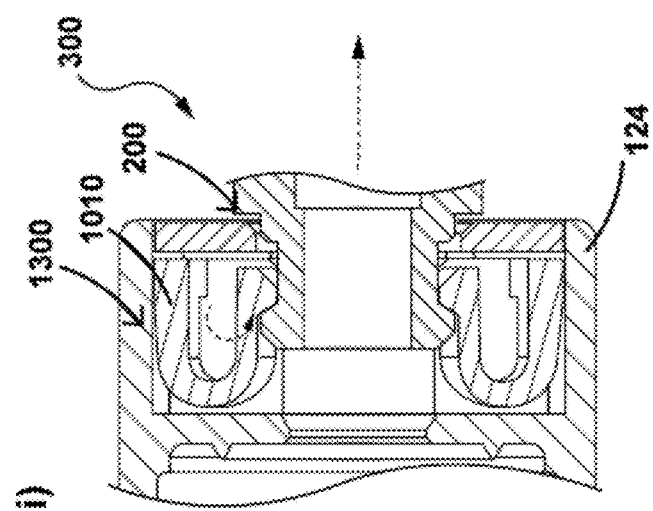
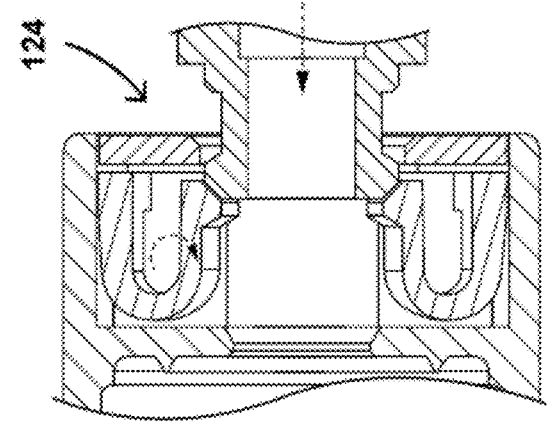
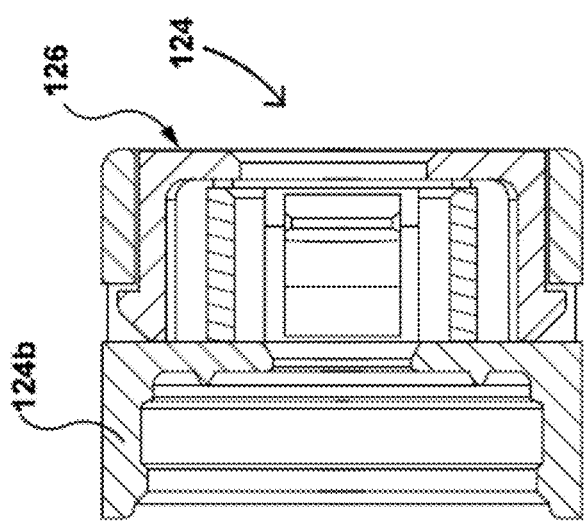
FIG. 5E(i)
FIG. 5E(ii)
FIG. 5F(i)
FIG. 5F(ii)

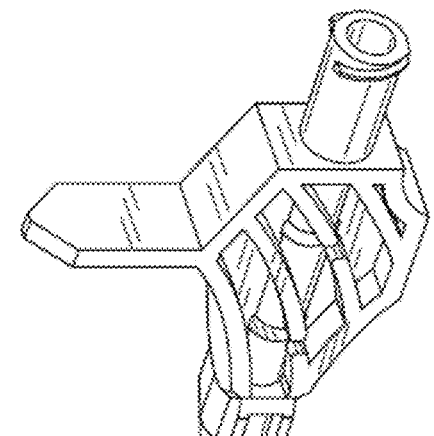
FIG. 6A(i)
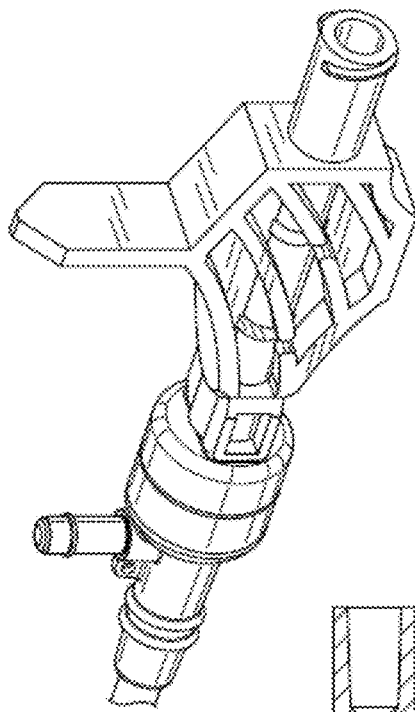
FIG. 6A(iv)
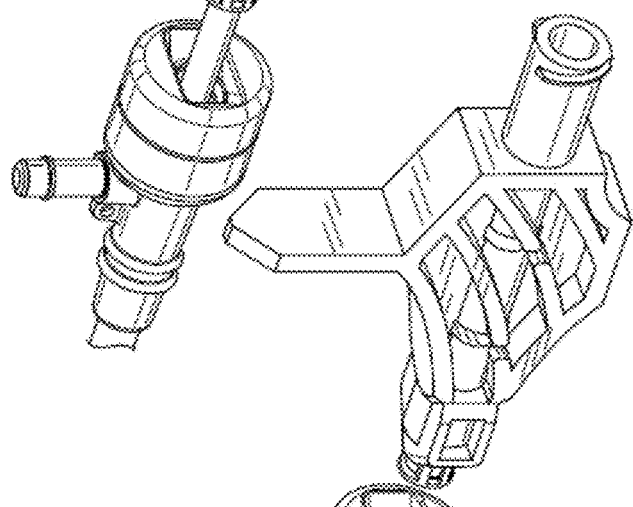
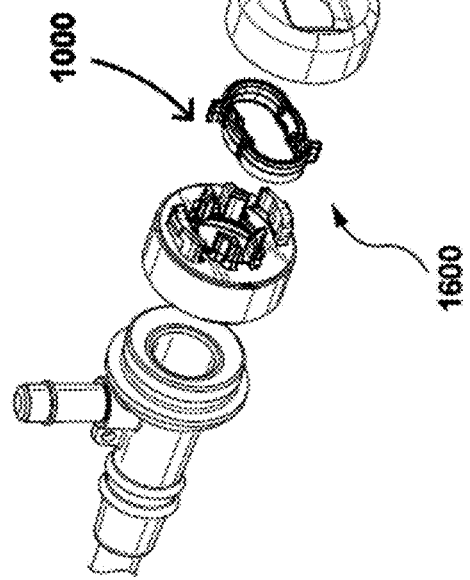
FIG. 6A(ii)
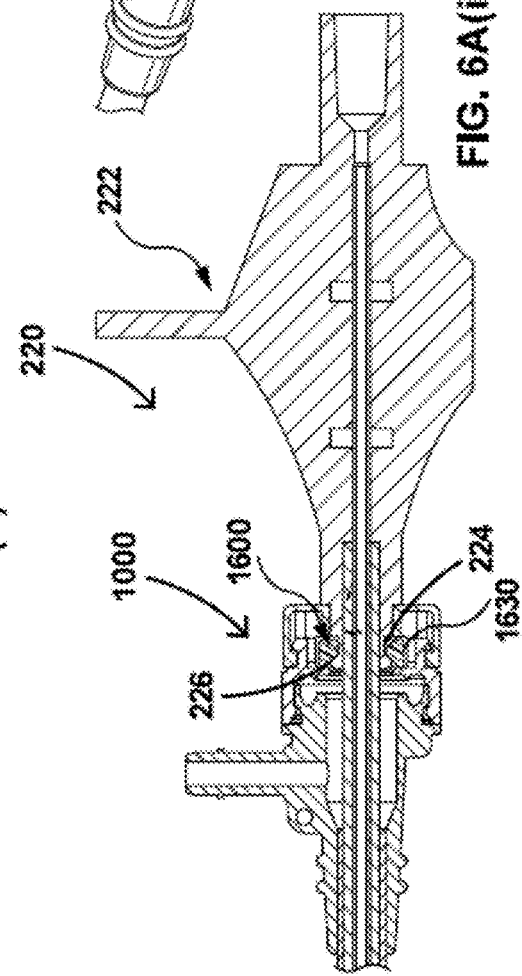
FIG. 6A(iii)

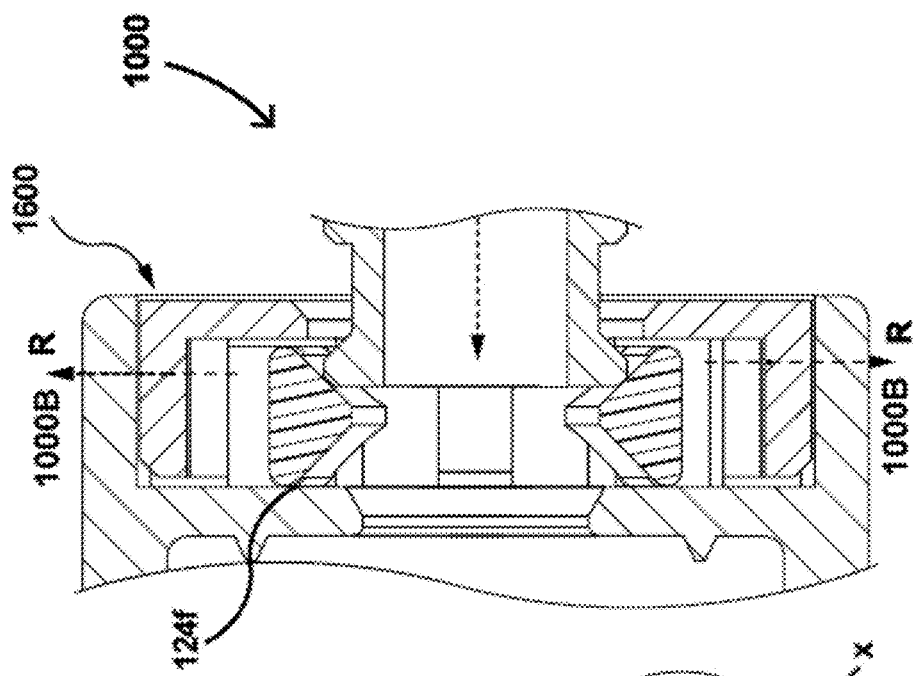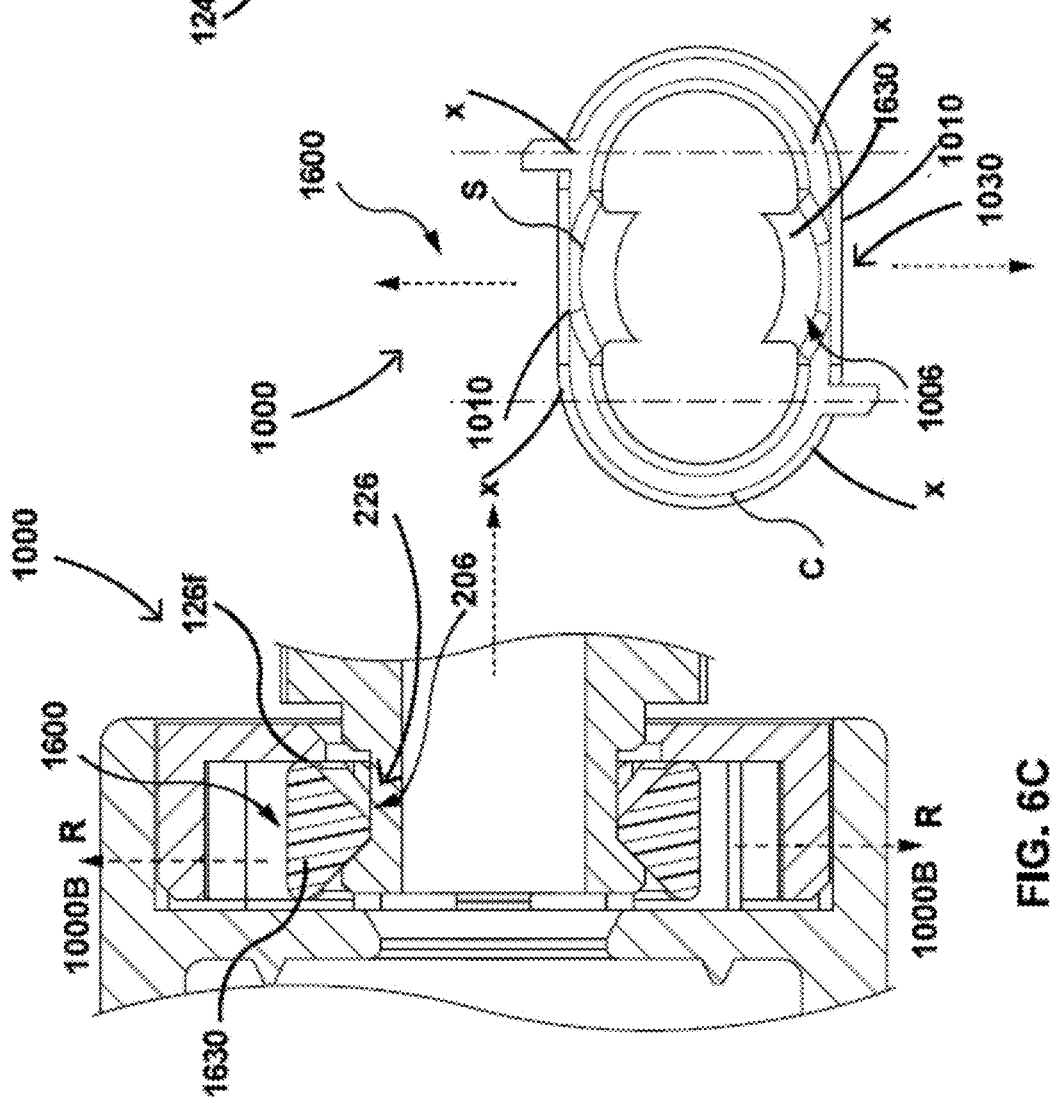
FIG. 6B
FIG. 6D(i)
FIG. 6C

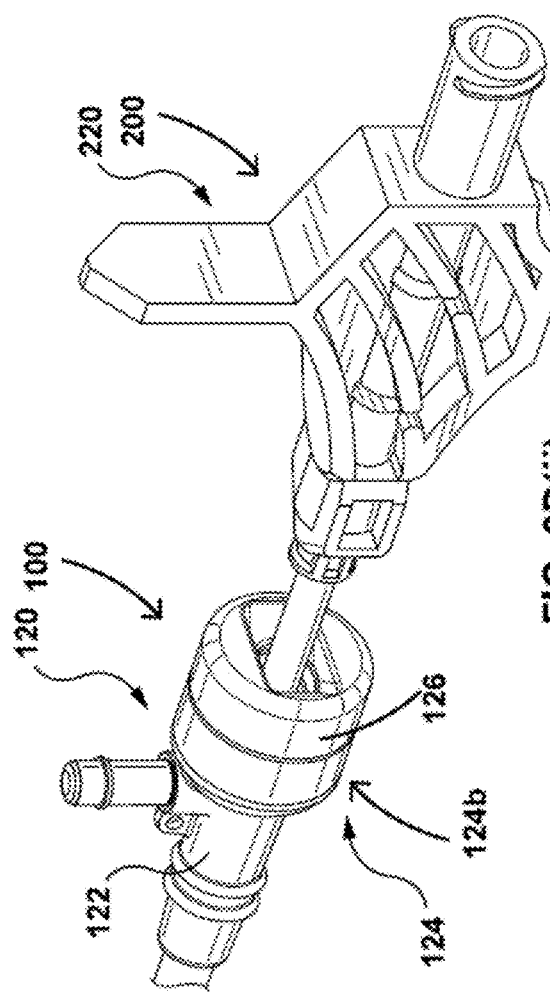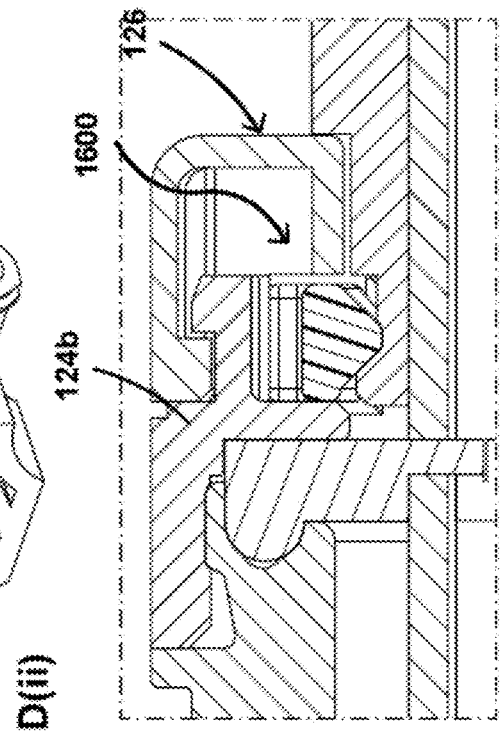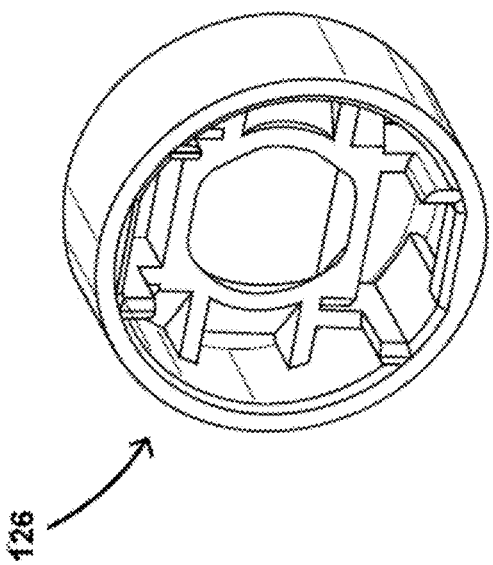

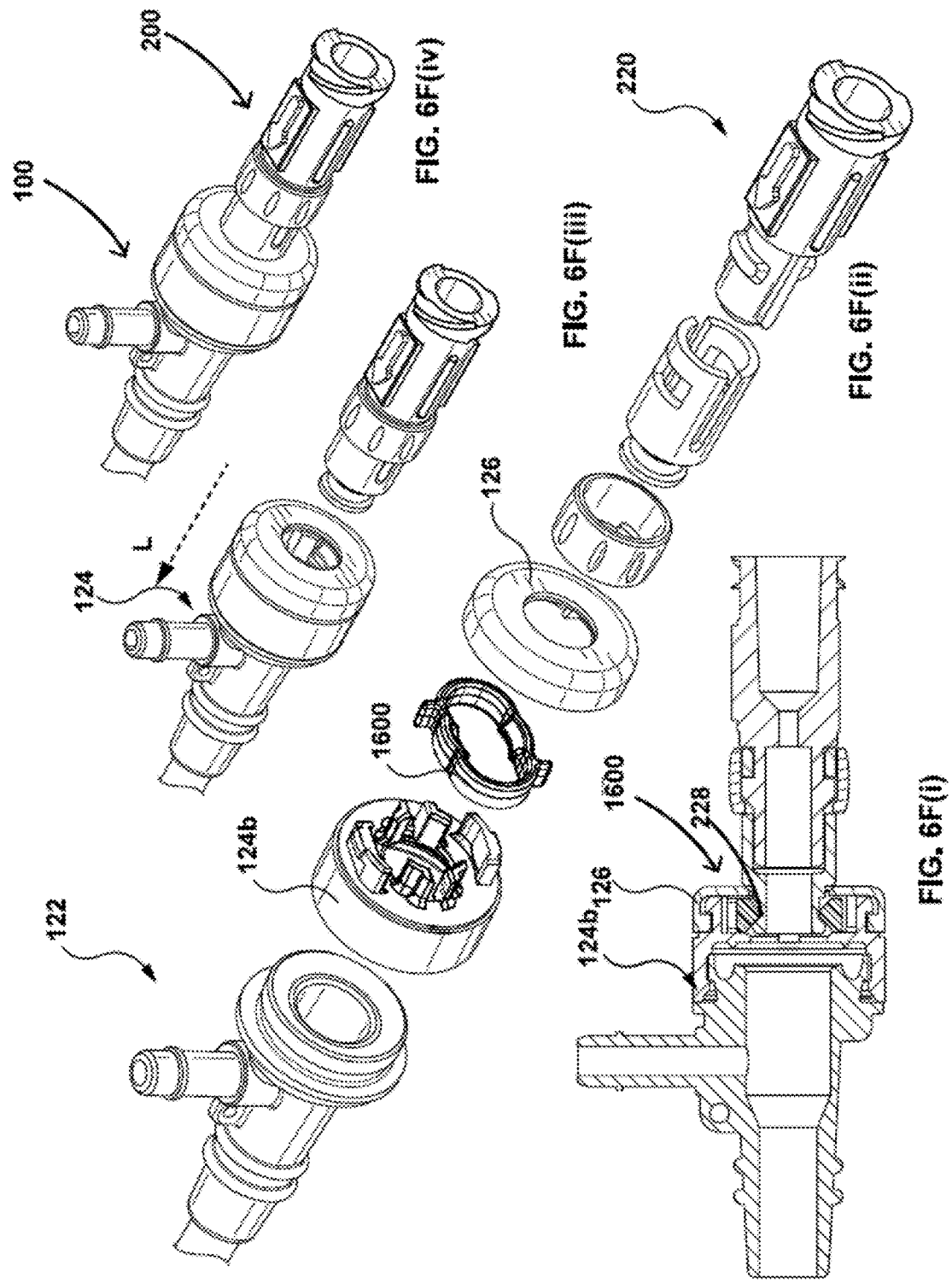

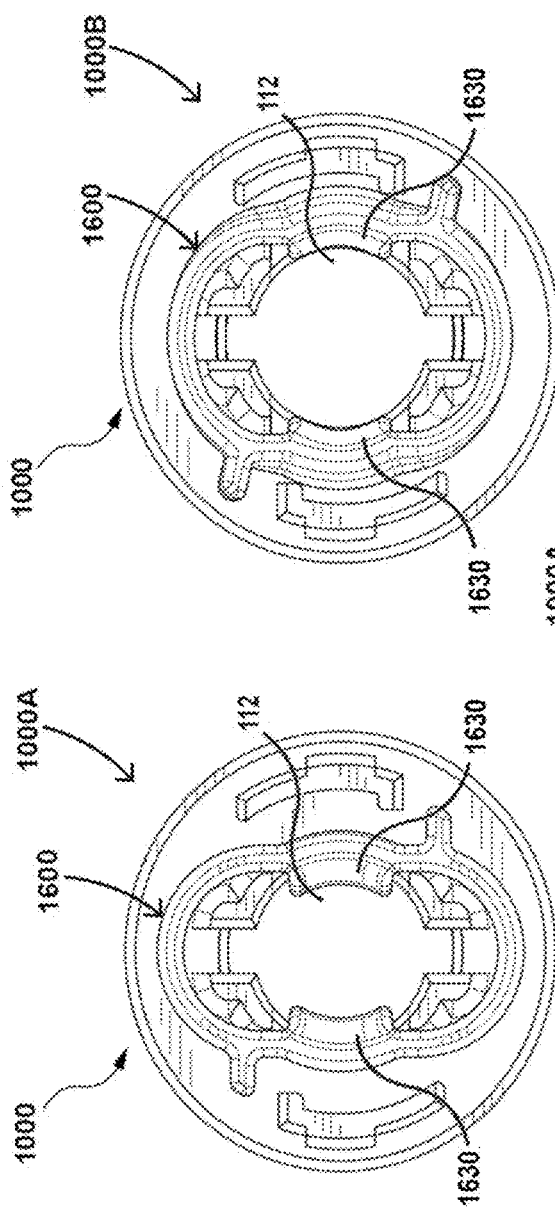
FIG. 7A
FIG. 7B
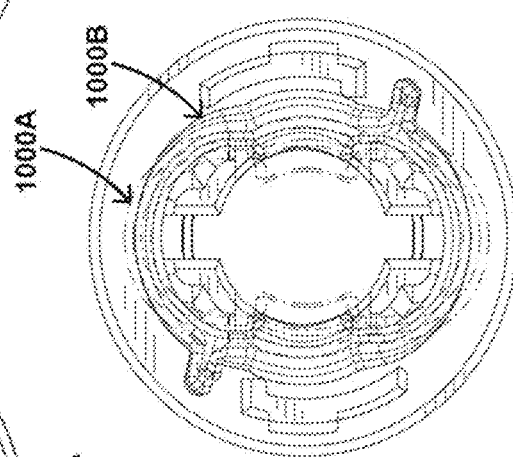
FIG. 7C
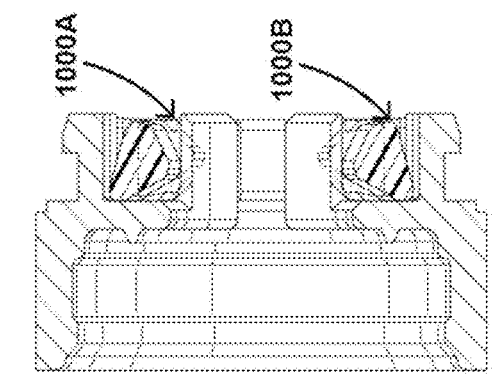
FIG. 7D

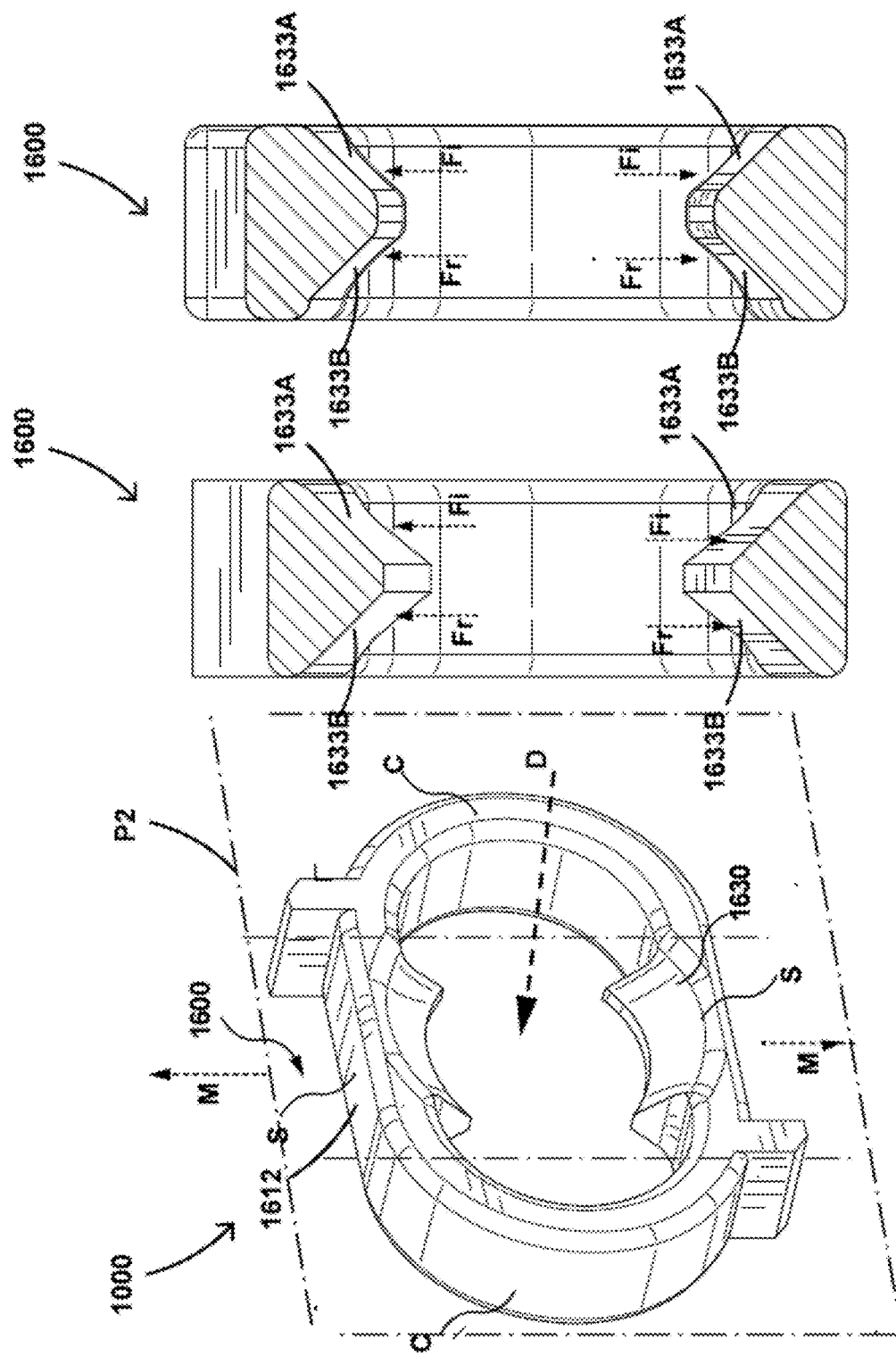

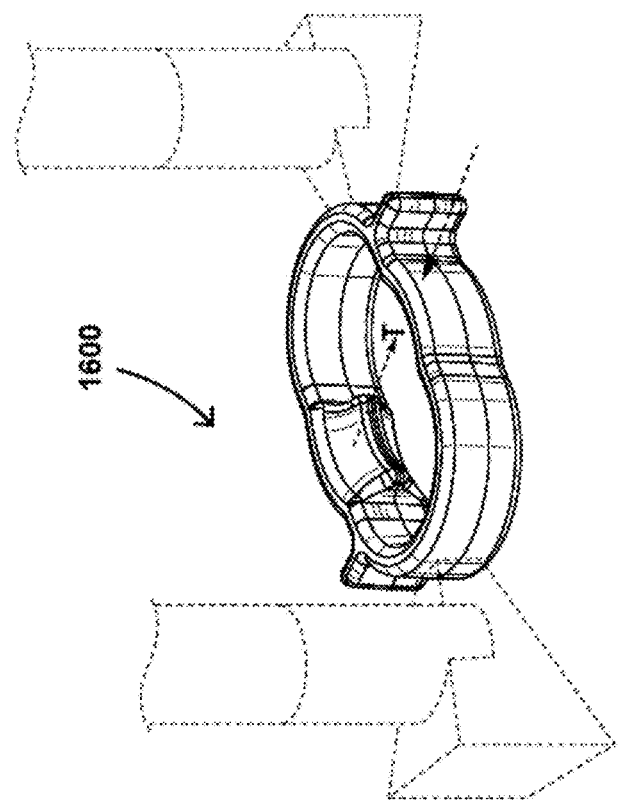
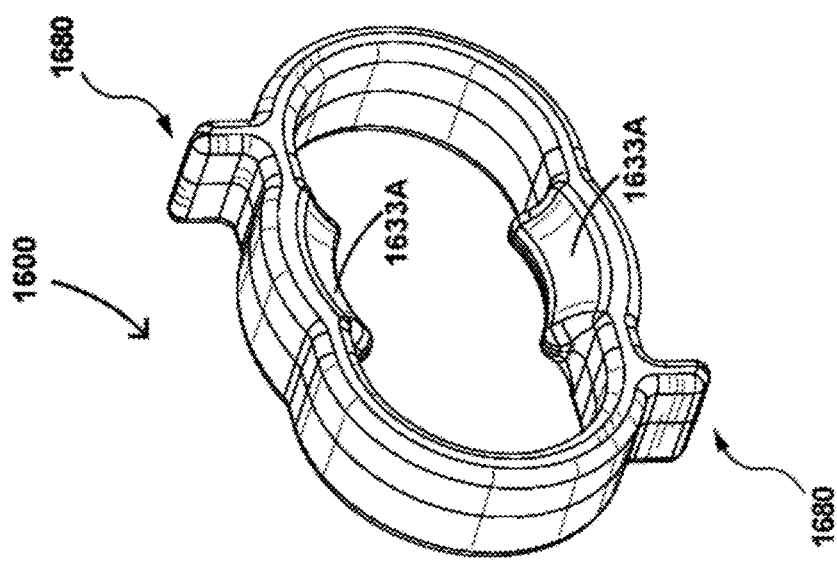
FIG. 8D(ii)
FIG. 8D(i)

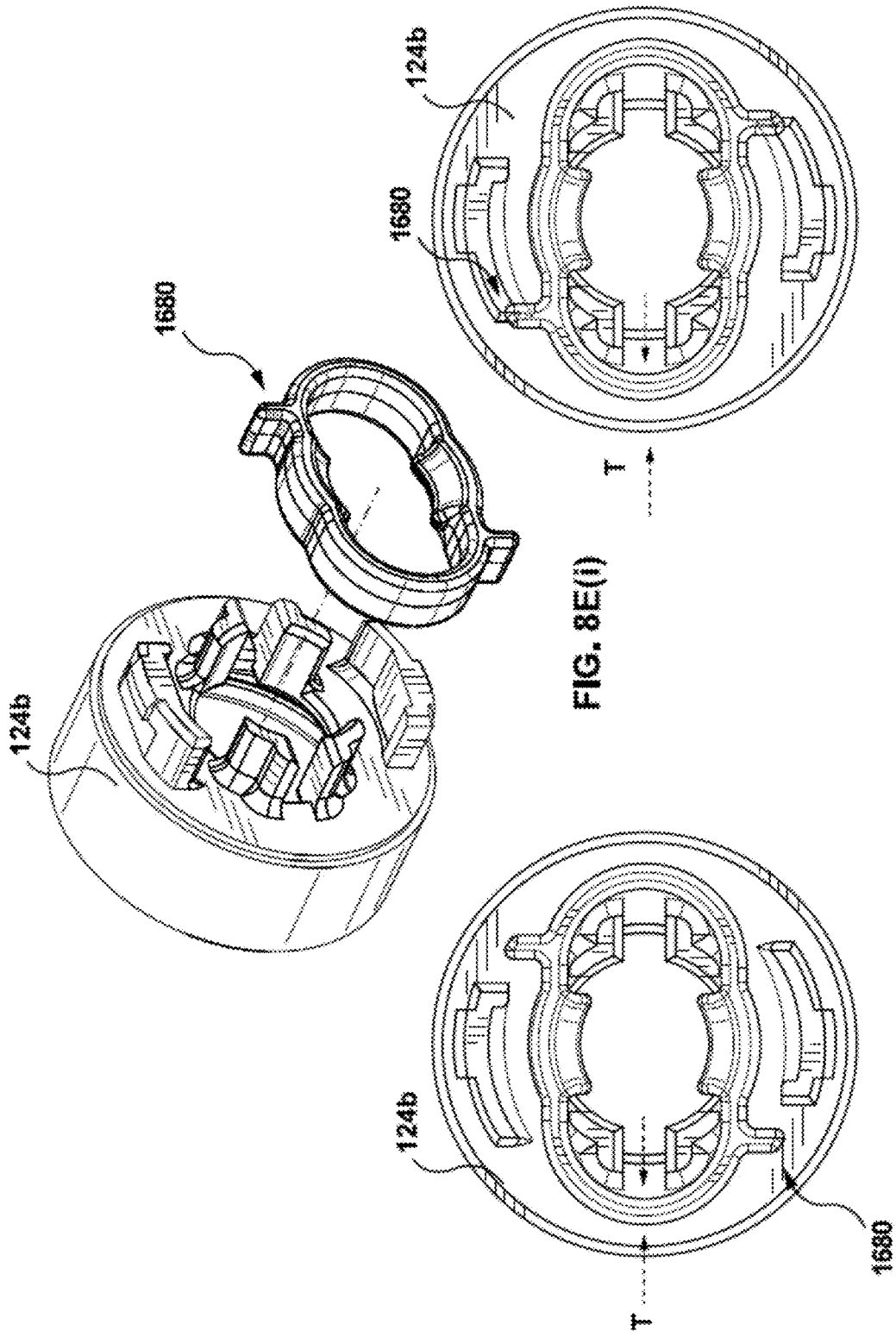

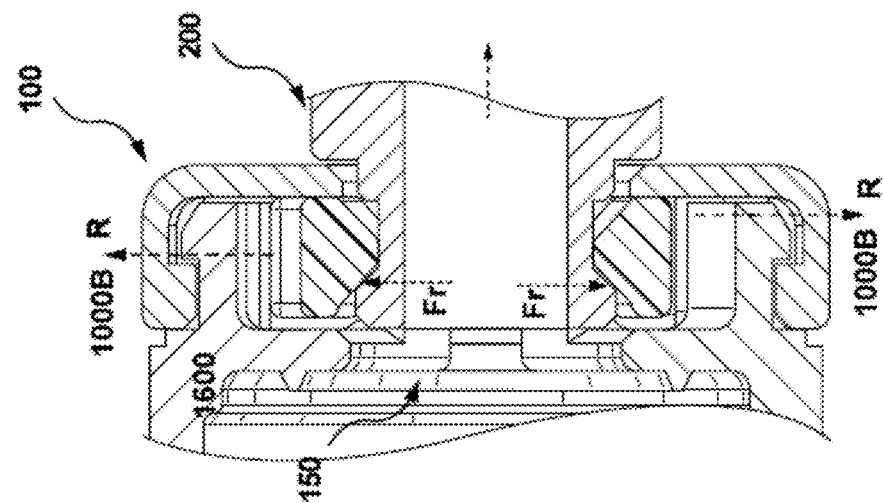
FIG. 8F(iii)
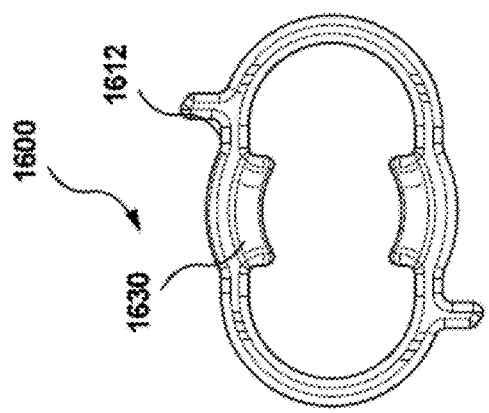
FIG. 8F(ii)
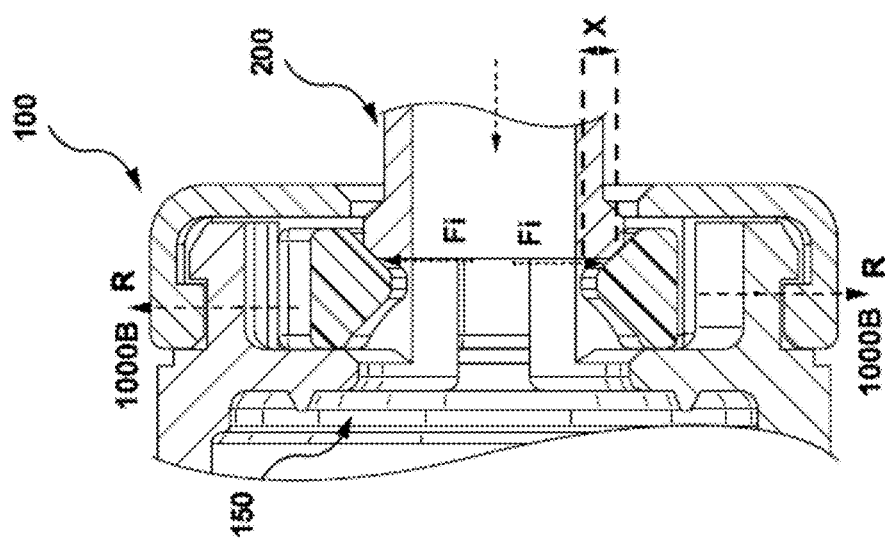
FIG. 8F(i)

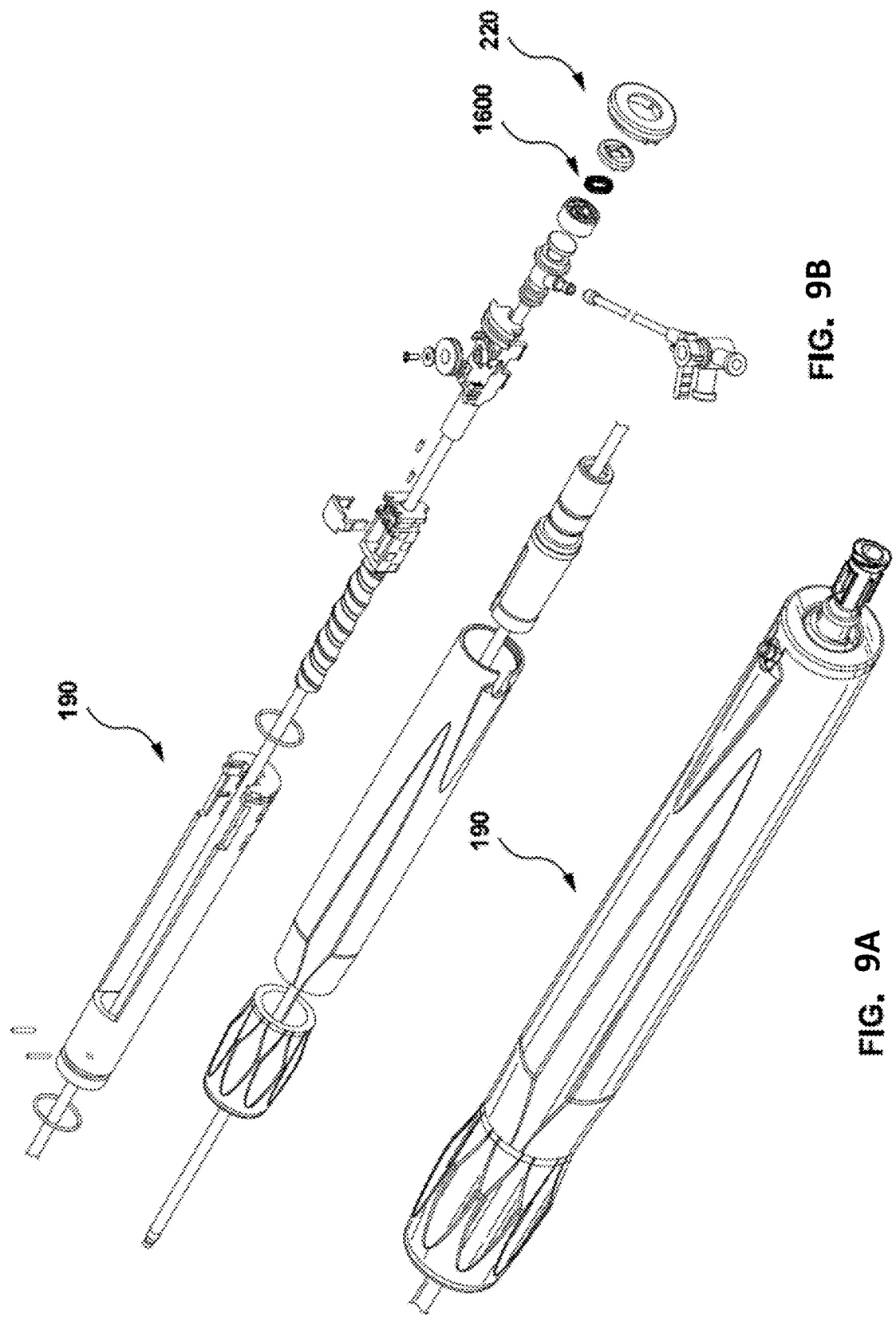

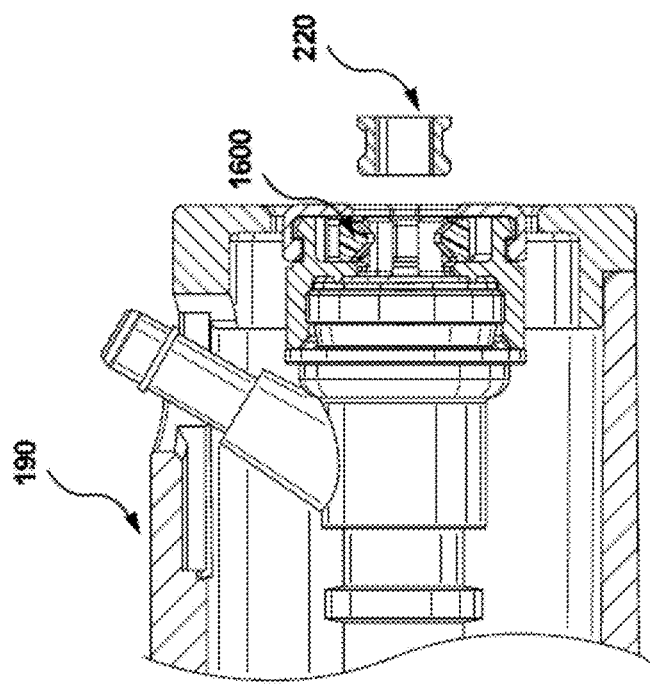
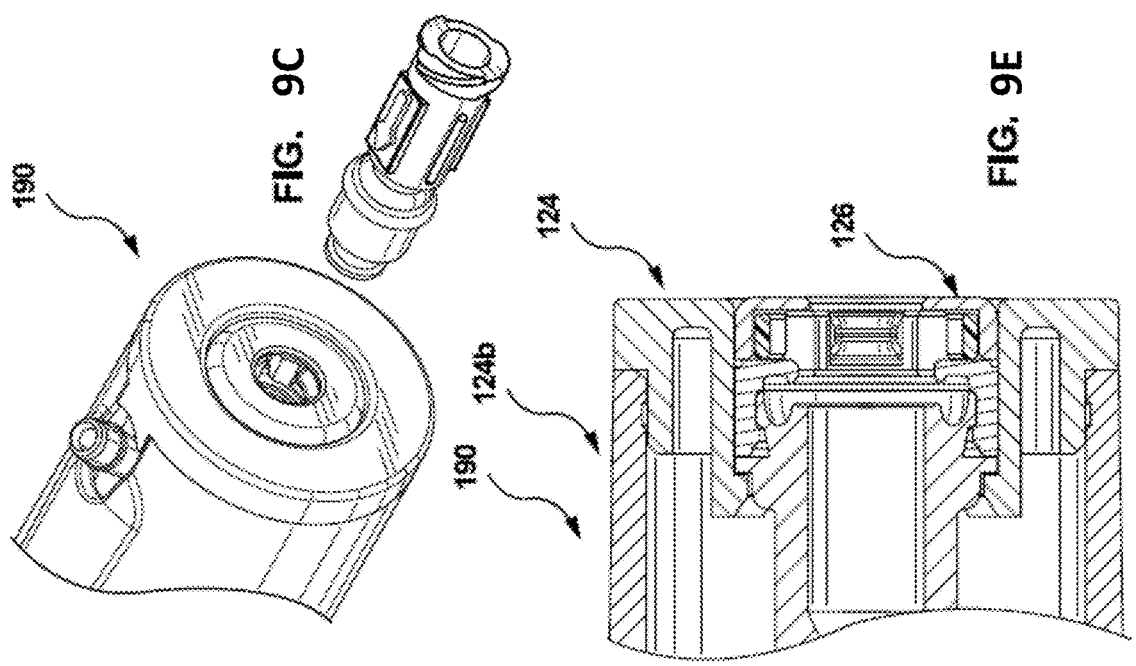

COUPLING MECHANISM FOR MEDICAL DEVICES

The disclosure relates to systems and methods that incorporate coupling mechanisms that allow for coupling two mating members, such as two medical devices, such as introducers, sheaths, dilators and the like for part of a procedure. More specifically, the disclosure relates to releasable coupling mechanisms, specifically snap-fit mechanisms, to allow for releasably coupling two medical devices such as a dilator and sheath for part of a procedure.

BRIEF DESCRIPTION OF THE DRAWINGS

In order that the invention may be readily understood, embodiments of the invention are illustrated by way of examples in the accompanying drawings, in which:

FIG. 2A(i) is a perspective view of a hub with a coupling mechanism, showing another device about to be inserted into the hub;

FIG. 2A(ii) is a cross sectional view of the hub of FIG. 2A(i), showing the other device partially inserted through the coupling mechanism;

FIG. 2B(i) is a perspective view of a hub with a coupling mechanism, showing another device about to be inserted into the hub;

FIG. 2B(ii) is a cross sectional view of the hub of FIG. 2B(i), showing the other device partially inserted through the coupling mechanism;

FIGS. 3A(i), 3A(ii) and 3A(iii) are, respectively, an exploded view, a perspective view and a cross section through a hub containing an embodiment of a coupling mechanism of the present invention;

FIGS. 3B and 3C are, respectively, cross sectional views of a device being inserted through an embodiment of a coupling mechanism and the device being retracted therefrom;

FIGS. 3D(i) and 3D(ii) are perspective exploded views illustrating various features of a hub and coupling mechanism of the present invention;

FIGS. 4A(i), 4A(ii) and 4A(iii) are, respectively, an exploded view, a perspective view and a cross section through a hub containing an embodiment of a coupling mechanism of the present invention;

FIG. 4A(iv) is a perspective view of an embodiment of a hub and coupling mechanism of the present invention;

FIGS. 4B and 4C, respectively, are cross sectional views showing a device that is being inserted through an embodiment of a coupling mechanism, and the device being removed from the coupling mechanism;

FIGS. 5A(i), 5A(ii) and 5A(iii) are, respectively, a perspective view, an exploded view, and a cross section through a hub containing an embodiment of a coupling mechanism of the present invention, as well as a device inserted through the coupling mechanism;

FIG. 5A(iv) is a perspective view of an embodiment of a hub and coupling mechanism of the present invention;

FIGS. 5B and 5C, respectively, are cross sectional views showing a device being inserted through an alternate embodiment of a coupling mechanism, and the device being removed from the coupling mechanism;

FIGS. 5D(i), 5D(ii) and 5D(iii) are, respectively, an exploded view, a perspective view and a cross section through a hub containing an embodiment of a coupling mechanism of the present invention;

FIG. 5D(iv) is a perspective view of an embodiment of a hub and coupling mechanism of the present invention;

FIGS. 5E(i) and 5E(ii) show, respectively, cross sectional and perspective views of an embodiment of a housing and a coupling mechanism of the present invention;

FIGS. 5F(i) and 5F(ii) are cross sectional illustrations of a device being inserted through an embodiment of a coupling mechanism of the present invention and being removed therefrom;

FIGS. 6A(i) and 6A(iv) are, respectively, perspective views of a device partially and fully inserted into a hub comprising an embodiment of a coupling mechanism of the present invention;

FIGS. 6A(ii) and 6A(iii) are, respectively, an exploded view and a cross section through a hub containing an embodiment of a coupling mechanism of the present invention, as well as a device inserted through the coupling mechanism;

FIGS. 6B and 6C are, respectively, cross sectional views of a device inserted through an alternate embodiment of a coupling mechanism of the present invention and being removed therefrom;

FIG. 6D(i) is a side view of an alternative embodiment of a coupling mechanism of the present invention;

FIG. 6D(ii) shows a perspective view of a device partially inserted through an embodiment of a coupling mechanism of the present invention;

FIG. 6E(i) shows a side view of an embodiment of a cap of a hub;

FIG. 6E(ii) is a partial cross sectional view of an alternate embodiment of a coupling mechanism located within a hub;

FIGS. 6F(i) and 6F(ii) are, respectively, a cross section through, and an exploded view of, a hub containing an embodiment of a coupling mechanism of the present invention, as well as a device inserted through the coupling mechanism;

FIGS. 6F(iii) and 6F(iv) are, respectively, perspective views of a device being inserted into a hub and being removed therefrom comprising an embodiment of a coupling mechanism of the present invention;

FIGS. 7A, 7B and 7C illustrate top views of a coupling member in accordance with an embodiment of the present invention in its different states;

FIG. 7D illustrates a side cross sectional view of a coupling member in accordance with an embodiment of the present invention in its different states;

FIG. 8A is a perspective view of a coupling member in accordance with an alternative embodiment of the present invention;

FIGS. 8B and 8C are different cross sectional views of the coupling member taken along the mid-point of the coupling member of FIG. 8A, in accordance with an alternative embodiment of the present invention.

FIGS. 8D(i) and 8D(ii) are a perspective view of a coupling member in accordance with an alternative embodiment of the present invention;

FIGS. 8E(i), and 8E(iii) are a top view of a coupling member in accordance with an embodiment of the present invention and a portion of the housing for retaining the same;

FIG. 8E(ii) is a perspective view of a coupling member in accordance with an alternative embodiment of the present invention as well as a portion of the housing for retaining the same;

FIGS. 8F(i), and 8F(iii) are, respectively, cross sectional views of a device inserted through an alternate embodiment of a coupling mechanism of the present invention and being removed therefrom;

FIG. 8F(ii) is a perspective view of a coupling member in accordance with an alternative embodiment of the present invention as well as a portion of the housing for retaining the same;

FIGS. 9A and 9B are, respectively, an exploded view and a perspective view of an alternate embodiment of the first mating member containing an embodiment of a coupling mechanism of the present invention, as well as a device inserted through the coupling mechanism;

FIG. 9C is a perspective view of an alternate embodiment of the first mating member comprising an embodiment of a coupling mechanism of the present invention, in accordance with an embodiment of the present invention;

FIGS. 9D and 9E are cross sectional views taken along different sections of the second mating member shown in FIG. 9C, that comprises an embodiment of a coupling mechanism of the present invention, as well as a device inserted through the coupling mechanism, in accordance with an embodiment of the present invention;

DETAILED DESCRIPTION

Figure 1A:
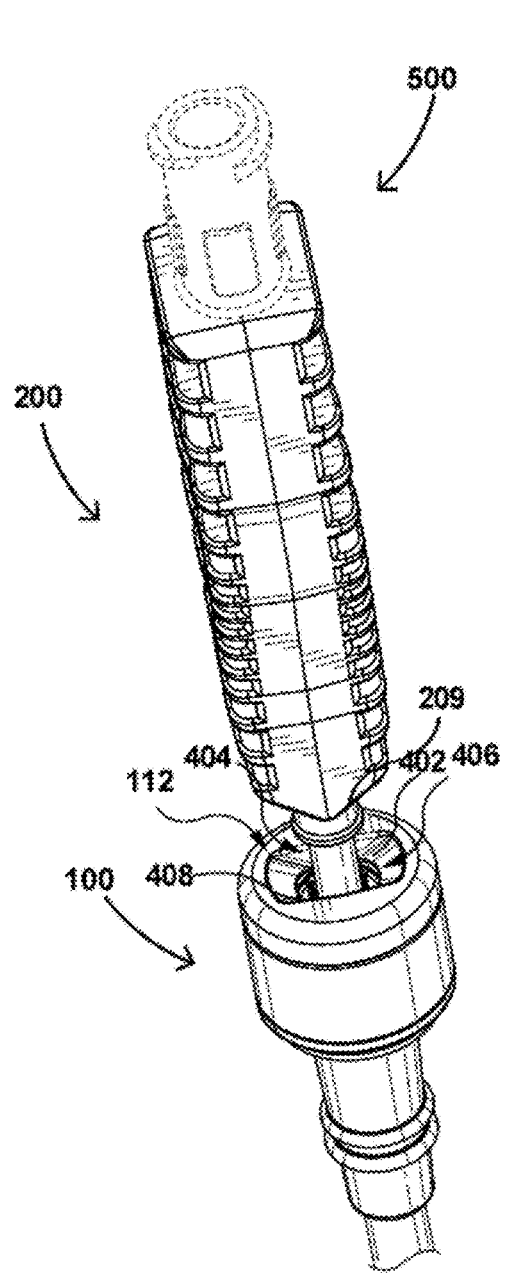
FIG. 1A is a perspective view of a hub for a medical device, comprising a coupling mechanism in accordance with an embodiment of the present invention and further showing a second device at least partially inserted into the hub.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In order to carry out certain medical procedures, such as trans-septal procedures, it is necessary to gain access to the heart specifically to the left atrium of the heart. Access may be obtained to the heart from vasculature using one or more medical devices, such as an introducer or sheath. In order to gain access, a superior approach may be used (by gaining access to the heart, for example from the jugular vein through the superior vena cava), or alternatively access may be obtained from the femoral or inferior approach (by gaining access to the heart from the femoral vein through the inferior vena cava). Once access is obtained into the left atrium, one or more additional devices may be advanced through the introducer or sheath to carry out a part of the procedure. For example, in order to carry out a trans-septal puncture, a puncture device is advanced through vasculature in order to puncture a septum of the heart to gain access to the left atrium. In some cases, the puncture device may be advanced through or with a sheath and dilator. Once the puncture device has punctured the septum, a dilator may be advanced to dilate the hole. This allows larger medical devices to be advanced through the puncture. In such procedures, the dilator may be locked or coupled to an introducer or sheath using a coupling mechanism during a portion of the procedure, allowing the two devices to be advanced concurrently and/or to enable two of the devices to be coupled together once they are properly positioned relative to one another. The coupling mechanism may also be decoupled during a part of the procedure so that the devices may be advanced independently.

In conventional systems, coupling mechanisms are provided that connect two devices at the proximal portions, thereof for example, along the hub portions, which ensures that the distal portions remain fixed in the desired position while the user guides the sheath and dilator inside the patient anatomy. In some such examples, the direction of the sheath curve is indicated by the side port on the sheath hub and is controlled by rotating the sheath hub. The coupling mechanism couples the dilator to the sheath allowing the sheath and dilator to be advanced and/or rotated together.

For example, once the devices are positioned at the septum prior to puncture, the dilator snaps into the sheath hub to connect the two devices. This is done by the user on the proximal end. By connecting the two devices proximally, it ensures the distal portions remain fixed in the desired position relative to one another while the user guides the sheath and dilator.

Certain limitations may be associated with the use of medical devices, such as introducers, sheaths, and dilators, that employ conventional coupling mechanisms, such as snaps. The limitations of the existing coupling mechanisms on these devices are that the snaps degrade with use, which may result in one or more of the following: insufficient retention force, insufficient tactile feedback, and/or generation of debris. Additionally, the coupling mechanism may not provide desired insertion force and/or removal force. In some such examples, it may be too difficult to, or require too much force to, snap or connect the two devices together, leading to difficulty when coupling the two devices. Similarly, it may require too much force to unsnap or disconnect the two devices which could lead to loss of positioning of the devices. Conversely, it may be too easy to, or require very little force to, snap or connect the two devices together.

Similarly, it may require very little force to unsnap or disconnect the two devices, providing insufficient retention force, and potentially leading to undesired and/or unintentional decoupling of the devices.

Conventional snap mechanisms require the use of plastic deformation, where the snaps are designed to, and require that, they deform plastically to enable coupling or locking of the two components. Such mechanisms rely on degradation of the snap component to enable locking. The degradation of components results in the components not retaining their shape over multiple uses, leading to the component becoming deformed or degraded over time. For example, a press fit between rigid rings, bumps, or tabs, may be used to couple two medical devices. As such, the initial insertion force value to enable coupling or locking for the first time may be high, however with multiple uses (even as early as the second or third use) the insertion force required to insert the dilator hub into the sheath hub may begin to decline rapidly. The user may need to use a very high force to snap the two devices initially but as the components degrade with multiple uses, the user will get a different feel, providing a varying and inconsistent user experience. The prior art snaps require the user to use a varying amount of insertion force to couple the sheath and dilator hubs together to snap the two hubs together. This provides the user with varying feedback on the force that is required in order to snap the two components together.

There exists a need to provide a coupling mechanism allowing two devices to be coupled together, while providing a relatively uniform insertion force and/or removal force. Furthermore, the coupling mechanism should not degrade with multiple uses, as well as, provide sufficient retention force and tactile feedback.

Inventors of the present invention have developed a novel locking or coupling mechanism for coupling or locking two medical devices and a system that uses the same. The novel mechanism as provided herein is a releasable coupling or locking mechanism that provides a coupling member or element such as a flexible coupling member that provides a flexible coupling at the interface between the two devices, for example at the interface between the proximal portion of the two devices. In other words, in some embodiments of the present invention, a flexible coupling member is provided that allows first and second mating members of a coupling system or arrangement to be releasably coupled to one another.

In one broad aspect, embodiments of the present invention include a releasable coupling mechanism for coupling a delivery catheter and a dilator. The delivery catheter comprising a first mating member and the dilator comprising a second mating member. The second mating member is positioned at a proximal end of the dilator and comprises a distal end and a proximal end. The first mating member positioned at a proximal end of the delivery catheter comprising a distal end and a proximal end. The proximal end of the first mating member comprises a first coupling means for releasably receiving a second coupling means which is positioned at a distal end of the second mating member. The first mating member further comprising a coupling member proximal of the proximal end of the first mating member; the coupling member comprising a pair of engagement members positioned on opposing sides of the coupling member and configured to releasably engage the second coupling means. The first mating member further comprising at least one indicia perpendicular from the pair of engagement members. The indicia indicate an orientation of the first mating member such that the second mating member disengages from the coupling member by simultaneously deflecting the pair of engagement members.

As a feature of this aspect, some embodiments include indicia comprising tactile indicia, visual indicia, or a combination of tactile and visual indicia. In some such embodiments, the tactile and visual indicia is at least one beveled edge.

In some embodiments of the present invention, the coupling mechanism is oval shaped with the pair of engagement members extending inwardly towards the center of the oval. In some such embodiments, the pair of engagement members then deflect in a radial direction.

In some embodiments, the pair of engagement members are configured to deflect from a first state to a second state upon insertion of the second mating member, wherein the distance between the pair of engagement members in the first state is less than the distance between the engagement members in the second state. In some such embodiments, the engagement members are configured to return to the first state upon removal of the second mating member.

In another embodiment of the present invention, the second mating member comprises a lip at the distal end, and a groove proximal to the lip. The groove has a diameter less than the diameter of the lip, wherein when the second mating member is inserted, the lip deflects the pair of engagement members from the first state to the second state. As the second mating member is inserted further, the pair of engagement members return to the first state, settling into the proximal groove, retaining the pair of engagement members and coupling the first mating member and second mating member, enabling the delivery catheter and the dilator to be advanced together throughout the transseptal procedure.

In some embodiments of the present invention, the first mating member is substantially oval in the first state and substantially circular in the second state.

In some embodiments of the present invention, the first mating member comprises a housing base and a cap, such that the coupling member is contained within the housing base and the cap. The cap comprises an aperture configured to receive the second mating member and the cap further comprises a beveled face from an outer edge to the aperture. In some embodiments of the present invention, the beveled surface on a distal portion of the second mating member corresponds to the beveled face, whereby the beveled surface on the distal portion of the second mating member is flushed.

In another broad aspect of the present invention, a delivery catheter for advancing through a patient's vasculature and delivery of medical devices, comprises a first mating member positioned at a proximal end of the delivery catheter. The first mating member comprises a distal end and a proximal end. The proximal end of the first mating member comprises a first coupling means configured to releasably receive a second coupling means positioned at a distal end of a second mating member, positioned at a proximal end of a dilator. The first mating member additionally comprises a coupling member proximal of the proximal end; the coupling member comprising a pair of engagement members positioned on opposing sides of the coupling member and configured to releasably engage the second coupling means. The first mating member includes at least one indicia, perpendicular from the pair of engagement members. The at least one indicia indicates an orientation of the first mating member such that the second mating member disengages from the coupling member by simultaneously deflecting the pair of engagement members.

In yet another broad aspect of the invention, a dilator for dilating a tissue and for use with a delivery catheter comprises, a second mating member positioned at a proximal end of the dilator. The second mating member comprises a second coupling means positioned at a distal end of the second mating member. The second coupling means is configured to be releasably inserted into a first coupling means of a first mating member. The first mating member is at a proximal end of the delivery catheter and wherein the first mating member comprises a coupling member proximal to the proximal end of the first mating member. The coupling member comprising a pair of engagement members positioned on opposing sides of the coupling member and configured to releasably engage the second coupling means. The first mating member comprises at least one indicia on the first mating member, perpendicular from the pair of engagement members; whereby the indicia indicates an orientation of the first mating member such that the second mating member disengages from the coupling member by simultaneously deflecting the pair of engagement members.

A Releasable Coupling Mechanism

Figure 1D:
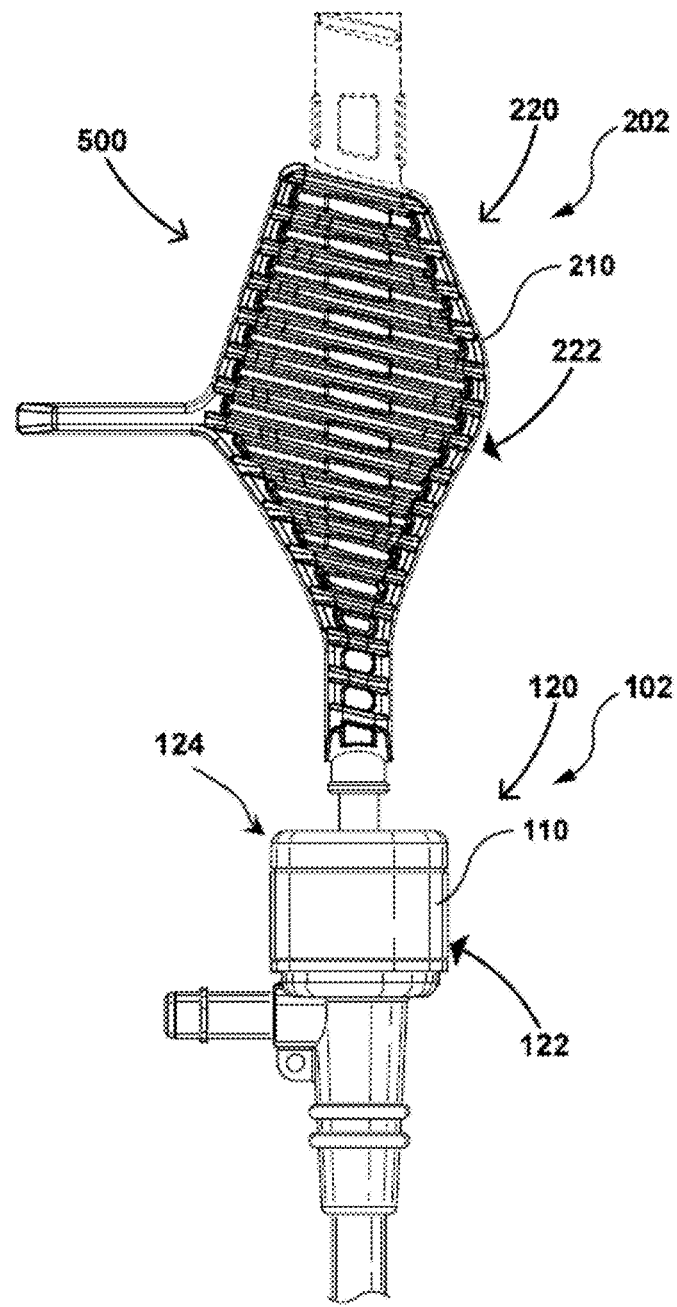
FIG. 1D is a side view of a device, for example a dilator, inserted into the hub of a second medical device, for example a sheath, wherein the sheath comprises a coupling mechanism in accordance with an embodiment of the present invention.

In some embodiments of the present invention as shown in FIG. 1A, a releasable coupling mechanism 300 is provided for releasably coupling two members such as a first mating member 100 and a second mating member 200. As additionally shown in FIGS. 1B and 1C, the releasable coupling mechanism 300 comprises a coupling member or component 1000 associated with a first mating member 100 for releasably coupling or engaging a second mating member 200 to the first mating member 100, where the second mating member 200 is receivable by the first mating member 100, for example through an opening 112 thereof. In some such examples, the coupling member 1000 is positioned inside or held within the first mating member 100, as shown in FIG. 1B.

In some such embodiments, the coupling member 1000 has a first state 1000A and a second state 1000B (shown in FIGS. 7A-7B) and is moveable there-between to enable the second mating member 200 to be coupled to the first mating member 100. Specifically, the coupling member 1000 is moveable from the first state 1000A into a second state 1000B upon insertion of the second mating member 200 into the first mating member 100 to allow passage of the second mating member 200. The coupling member 1000 is moveable thereafter into the first state 1000A to couple the second mating member 200 to the first mating member 100, discussed further herein below.

The first state of the coupling member 1000 is the distance between the engagement members when no force is being applied to the coupling member. In an embodiment, the distance between the engagement members is less than the diameter of the opening 112 of the first mating member 100. For example, with reference to FIG. 7A, the distance between the engagement members, such as snaps 1630, of the oval shaped coupling member 1600 is less than the diameter of the opening 112. The second state of the coupling member 1000 is the distance between the engagement members when a force is being applied by a second mating member as it is being advanced therethrough. In this second state, the distance between the engagement members is substantially equivalent to (or greater than) the diameter of the opening of the first mating member. With reference now to FIG. 7B, the distance between the engagement members, such as snaps 1630, of the oval shaped coupling member 1600 is substantially equal to the diameter of the opening.

Releasable Coupling Assembly

Figure 1C:
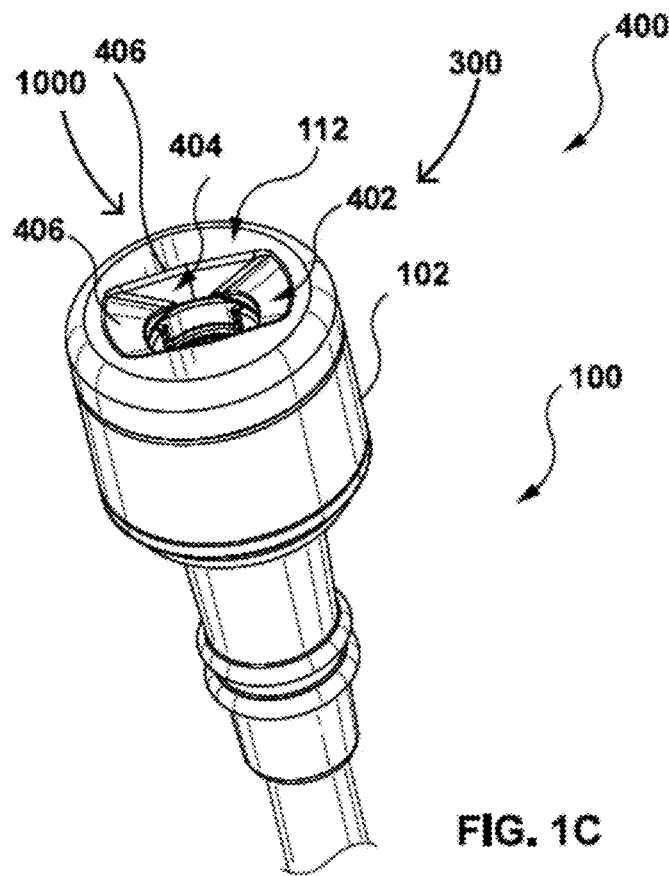
FIG. 1C is a perspective view of the hub, showing a coupling mechanism comprising guides and co-operating features for enabling coupling of two medical devices in accordance with an embodiment of the present invention.
Figure 1B:
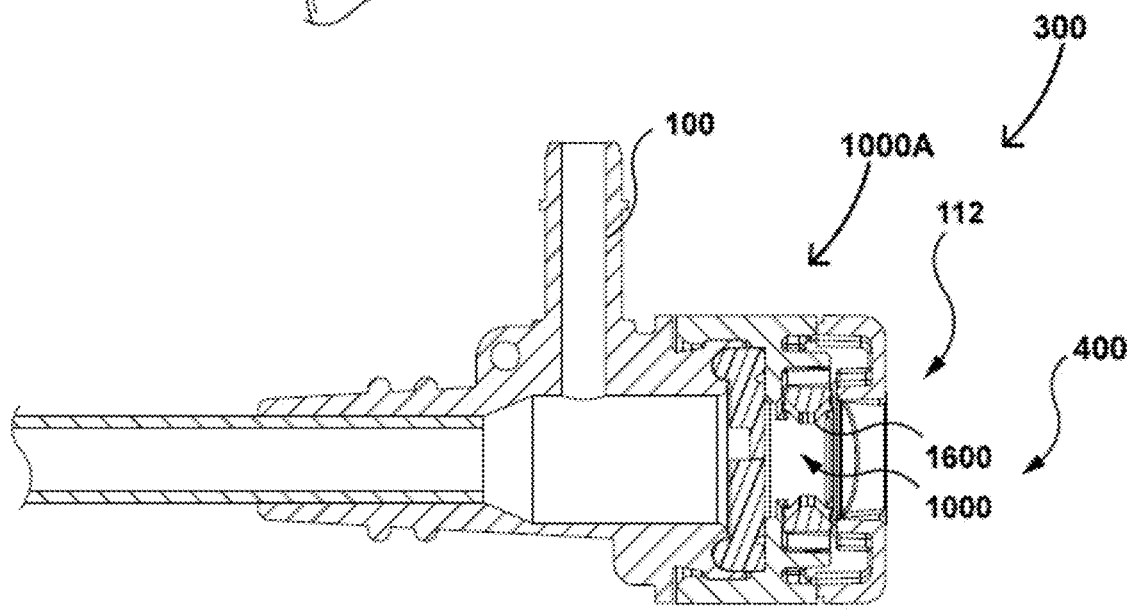
FIG. 1B shows a cross sectional view of the hub of FIG. 1A and the coupling mechanism incorporated therein, in accordance with an embodiment of the present invention.

In accordance with some embodiments of the present invention, a releasable coupling assembly 400 is provided that comprises the first mating member 100 and a coupling mechanism 300, as shown in FIGS. 1A-1C. More specifically, the releasable coupling assembly 400 comprises, the first mating member 100 and a coupling mechanism 300.

Releasable Coupling System

With reference to FIGS. 1A and 1D, a coupling system 500 comprises a first mating member 100, a coupling mechanism 300, wherein the coupling mechanism 300 comprises a coupling member 1000, and a second mating member 200. For example, the coupling system 500 comprises a releasable coupling mechanism 300 that allows for releasably coupling two medical devices 102, 202, such a delivery catheter, for example as a sheath 120, and a dilator 220.

In one such embodiment, the first mating member 100 comprises a handle portion 110, such as a handle on a sheath 120. With reference to FIG. 1A-1D, the handle 110 comprises a sheath hub 122 defining a housing 124; the housing 124 comprises an opening 112 for receiving the second mating member 200 positioned on a dilator 220. In some embodiments, the coupling member 1000 is coupled to the housing 124 of the first mating member 100. In an embodiment, the coupling member 1000 may not necessarily be directly attached or coupled to the housing 124 but is functional to interact with the housing 124 upon insertion or removal of a second mating member 200 from the first mating member 100.

The releasable coupling system 500 additionally comprises a second mating member 200 that is configured to be inserted within and received by the first mating member 100. In some such embodiments, the second mating member 200 comprises a handle portion 210 of a second device 202 (see, for example, a dilator 220 shown in FIGS. 1C and 1D) that is received by the opening 112 of the first mating member 100 of a first device (see, for example, a sheath 120). The handle portion 210 comprises a dilator hub 222 comprising a wider portion 226 (for example such as ridge, a lip, a bump, or a ring 228), and a handle groove portion 224 (as shown in FIGS. 2A(i), 2A(ii)) for receiving a portion of the coupling member 1000. For example, as illustrated in FIG. 6A(iii), the groove portion 224 would receive the snaps 1630 of an oval shaped coupling member 1600.

In accordance with a releasable coupling system 500 of the present invention, the coupling member 1000 defines a first corresponding co-operative feature 1006 (as shown in FIG. 6D(i)). The first corresponding co-operative feature 1006 comprises engagement members, such as snaps 1030 (also indicated as 1630 on FIG. 6D(i)). A second corresponding co-operative feature 206 is provided on the second mating member 200. In some examples, the second mating member 200 comprises a groove 226, as shown in FIGS. 6B and 2A(i)-2A(ii). The first corresponding co-operative feature 1006 of the coupling member 1000 is operable to co-operatively engage the second corresponding co-operative feature 206 of the second mating member 200 for releasably coupling the first and second mating members 100, 200.

In some such embodiments of the releasable coupling system 500, the releasable coupling mechanism 300 comprises a translational locking mechanism. For example, in the case of a sheath 120, a housing base portion 124*b* and sheath hub cap 126 define the housing 124. The sheath hub 122 comprises a hub portion 125 that is coupled to the housing 124. The housing 124 interacts with the coupling member 1000 to prevent translational movement of the second mating member 200 with respect to the first mating member 100. As shown in FIGS. 6A(iii) and 6A(iv), the coupling member 1000 interacts by co-operatively engaging (at least functionally) with the second mating member 200 The housing 124 interacts to prevent movement of the coupling member 1000 translationally in the proximal and distal directions. Specifically, the sheath hub cap 126 prevents proximal retraction of the second mating member 200 and the housing base portion 124b prevents distal movement of the second mating member 200, thereby preventing further advancement.

General Coupling Member Housing

As described herein above, some embodiments of the present invention provide a releasable coupling mechanism 300 which comprises a housing 124 of the first mating member 100. The coupling member 1000 is functionally coupled to the housing 124 of the first mating member 100 to retain the second mating member 200 once it is inserted into the housing 124. For example, as shown in FIGS. 1A-1D, the coupling member 1000 is held within the housing 124 of the first mating member 100. The coupling member 1000 is configured to interact with the housing 124 to prevent removal of the second mating member 200 in the absence of force and to prevent translational movement of the coupling member 1000. In an embodiment, the coupling member 1000 abuts against the proximal inner surface of the housing 124 or a distal inner surface of the housing 124 to prevent translation thereof.

In some such examples, the coupling member 1000 is attached to the housing 124. These examples are shown in FIGS. 2A-2B, as well as FIGS. 3A-3C, 4A-4C, FIGS. 5A-5F.

Engagement Member of the Coupling Member

The coupling member 1000 of the coupling mechanism 300 comprises at least two engagement members. The at least two engagement members may be protrusions, such as snaps, extending from a surface of a straight cantilever, a u-shaped cantilever, or retaining arms.

Straight Cantilever Embodiment

With specific reference now to FIGS. 2A(i)-2A(ii), and 2B(i)-2B(ii), the coupling member 1000 is formed integrally with the housing 124 of the first mating member 100. In some such embodiments of a releasable coupling mechanism 300, the coupling member 1000 comprises at least one cantilever 1010. The at least one cantilever 1010 comprises at least one straight cantilever 1200 and is formed integrally with the housing 124, for example with a cap 126. In an embodiment, the straight cantilever 1200 is movable from a first state 1000A (as shown in FIG. 2A(i)), into a second state 1000B (as shown by directional arrows R). This allows the second mating member 200 to pass through the opening 112 of the first mating member 100. The straight cantilever 1200 then returns to a first state 1000A. The at least one straight cantilever comprises one or more retaining arms 1212 as shown in FIG. 2A(i). In some such embodiments, the one or more retaining arms 1212 terminate in one or more engagement members, for example snaps 1230. With regards to FIG. 2B(ii), the embodiment comprises two straight cantilevers 1200x, 1200y which are deflectable (i.e., deflect radially outward) to move from the first state 1000A into the second state 1000B upon insertion of the second mating member 200. The straight cantilevers 1200 are moveable in a plane P1 that is substantially in plane with the direction of advancement D of the secondary mating member 200 into the housing 124 for insertion therein. The two straight cantilevers 1200x, 1200y can return thereafter into the first state 1000A to couple the second mating member 200 to the first mating member 100.

U-shaped Cantilever Embodiment

With reference now to FIGS. 3A(i)-3C, 4A-4C, FIGS. 5A-5F, the at least one cantilever 1010 are u-shaped cantilevers 1300. With specific reference now to FIGS. 3A(i) and 3A(iii), as well as FIGS. 3D(i) and 3D(ii), the one or more u-shaped cantilevers 1300 are held within the housing 124. In some examples, the housing base portion 124b is coupled to a hub portion 125. The u-shaped cantilevers 1300 are held within and coupled to the housing base portion 124b. In some such embodiments, the u-shaped cantilevers 1300 are exposed along a proximal face, forming the proximal outer face of the first mating member 100 as shown in FIG. 3A(ii).

As shown in FIGS. 5A(i) and 5A(iii), the u-shaped cantilevers 1300 are substantially contained within or retained by the housing 124 (defined by the housing base 124b and cap 126). The housing base portion 124b is formed integrally with the hub cap 126, and thus the housing 124 of the first mating member 100, is formed integrally as a substantially unitary construction or piece. As such, the u-shaped cantilevers 1300 may be contained within the integrally formed housing 124.

Alternatively, as shown in FIGS. 5D(i)-5D(iv), the housing 124 is formed from a two parts, comprising a housing base 124b and a separate hub cap 126 that are coupled together for example using a snap fit arrangement (as shown in FIG. 5E(i)). As such, the housing 124 comprises a housing base 124b and hub cap 126 and the u-shaped cantilevers are contained within.

As shown in FIGS. 3A(i)-3D(ii), 4A(i)-4C, 5A(i)-5F(ii), the u-shaped cantilever 1300 comprises moveable cantilever arms 1312. In some examples, the u-shaped cantilevers 1300 are composed of a flexible material, enabling the cantilever arms 1312 to flex between the first state 1000A and the second state 1000B. For example, the u-shaped cantilevers 1300 are composed of an elastically deformable material, wherein the material remains in the elastic region of the strain curve. In an alternative embodiment, the u-shaped cantilevers 1300 may be composed of a resilient material.

The pair of u-shaped cantilevers 1300 are moveable in a plane P1 (as shown in FIG. 3B, 3C, 4B, 4C, 5B, 5C) that is substantially in plane with the direction D of advancement of secondary mating member into the housing for insertion or removal. Alternatively, in some embodiments, the pair of u-shaped cantilevers 1300 are moveable in a plane P2 that is perpendicular to the direction D of advancement of second mating member200 into the housing 124 for insertion or removal (into and out of FIG. 3B).

The u-shaped cantilevers 1300 have retaining snap arms 1312 that terminate engagement members, such as snaps 1330, as shown in FIGS. 3B, 3C, 4B, 4C and 5B, 5C. The snaps 1330 may comprise dual ramps 1333A, 1333B, where the first ramp 1333A defines an insertion ramp angle and the second ramp 1333B defines a removal ramp angle. The insertion ramp angle and removal ramp angle create a component of force required for insertion Fi and removal Fr that compresses the snaps 1330. In some such examples, the angles on the first and second ramps 1333A, 1333B may be varied to define respective insertion and removal forces. In some instances, the force may be varied by a moment created on the snap arm 1312. Specifically, as shown in FIGS. 3B, 5B and 5F(i), as the second mating member 200 is advanced into the first mating member 100, the insertion force Fi will create a moment on the snap arm 1312 which will increase the force required to move the u-shaped cantilever 1300 from its first state 1000A into its second state 1000B. In some embodiments, the u-shaped cantilever 1300, is effectively biased in first state 1000A, and the moment on the snap arm 1312 will effectively increase the force required to overcome this bias in order to move the u-shaped cantilever 1300 into its second state 1000B. Conversely, upon removal of the second mating member 200 from the first mating member 100 as shown in FIG. 3C (and additionally FIGS. 5C and 5F(ii)), the removal force will create a moment on the snap arm 1312, which will decrease the force required to move the u-shaped cantilever 1300 from its first state 1000A into its second state 1000B. In other words, the u-shaped cantilever 1300, is effectively biased in first state 1000A, and the moment on the snap arm 1312 will effectively decrease the force required to overcome this bias in order to move the u-shaped cantilever 1300 into its second state 1000B. In some such embodiments, the angle of the second or removal ramp 1333B may be provided as a relatively steep angle.

In other examples, the first and second ramps 1333A, 1333b have substantially equivalent ramp angles defining substantially equivalent insertion and removal forces Fi, Fr.

Inverted U-shaped Cantilever Embodiment

As illustrated in FIGS. 4A(i)-4A(iv), the u-shaped cantilevers 1300 comprises a pair of inverted u-shaped cantilevers 1302 which may be held within the housing 124, specifically the housing base portion 124b, and form the proximal face of the first mating member 100 (specifically with reference to FIG. 4A(iv)). As was previously discussed, the first ramp 1333A and second ramp 1333B may be different ramp angles, contributing to differing insertion and removal forces Fi, Fr. Conversely, the ramp angles 1333A, 1333B may be substantially equivalent providing a relatively uniform insertion and removal force Fi, Fr.

Oval Shaped Coupling Member Embodiment

As shown in FIGS. 6A(i)-6F(iv), 7A-7D, 8A-8F(iii), and 9A-9E, a releasable coupling member 1000 is retained within the housing 124. In the embodiments shown the coupling member 1000 is substantially free floating or loose within the housing 124. Specifically, with reference to FIGS. 6A(i)-6F(iv), the coupling member 1000 comprises at least cantilever 1010, as shown in FIG. 6D(i). The at least one cantilever 1010 may comprise a simply supported beam configuration. For example, two substantially straight segments S may be coupled together using one or more arcuate segments C, as shown in FIG. 8A. Each of the two straight segments S of the cantilevers 1010 are coupled together at each of their respective ends by an arcuate C segment. These substantially straight segments S, are deflectable portions that are defined by a simply supported beam configuration, where maximum deflection M is along the mid-point of the straight segments S. In some such examples, each of the deflectable portions comprise one or more retaining arms 1612 where the one or more retaining arms comprise one or more engagement members, such as snaps 1630.

In these types of embodiments, the coupling member 1000, may be formed as an oval shaped coupling member 1600, as illustrated in FIGS. 7A and 7B. The oval shaped coupling member 1600 comprises one or more retaining arms 1612 that terminate in one or more engagement members, for example snaps 1630. The oval shaped coupling member 1600 may be in the form of a snap ring or band 1601.

In the embodiments illustrated in FIGS. 6A(i)-6F(iv), 7A-7D, 8A-8F(iii), 9A-9E, the oval shaped coupling member 1600 is functionally coupled to the housing 124, while remaining unattached or unengaged during use so that it is moveable feely within the housing 124. Specifically, with reference to FIGS. 6D(ii), 6E(i) and 6E(ii), the oval shaped coupling member 1600 is housed within the base portion 124b of a sheath hub 122 and is retained by the sheath hub cap 126. As such, the combination of the housing base portion 124b and the sheath hub cap 126 form an enclosure to for the oval shaped coupling member 1600, as illustrated in FIG. 6F(i).

With reference now to FIGS. 6E(ii), and 6F(i) 6F(iv), the housing 124, as defined by housing base portion 124b and sheath hub cap 126, interacts with the oval shaped coupling member 1600 to prevent translational movement of the second mating member 200, with respect to the first mating member 100, once the second mating member 200 is inserted into the first mating member 100. In some such examples, the housing 124 interacts to prevent translational movement of the oval disc coupling member 1600 in the proximal and distal directions. Specifically, the sheath hub cap 126 prevents proximal retraction of the second mating member 200 and the base of the housing base portion 124b prevents distal movement of the mating member 200.

As shown in FIGS. 6B and 6C, the oval shaped coupling member 1600 and the snaps 1630 rub against the distal face 124f of the housing base portion 124b. The resulting friction will increase the insertion force as shown in FIG. 6B. Conversely, the oval shaped coupling member 1600 and the snaps 1630 rub against the proximal face 126f of the sheath hub cap 126. The resulting friction will increase the removal force.

The oval shaped coupling member 1600 may have an oval shaped configuration in its first state 1000A (FIG. 7A) and substantially round shaped configuration in its second state 1000B (FIG. 7B). The substantially oval shaped coupling member 1600, is deflectable to move (for example radially) from its oval shaped configuration in its first state 1000A into its round shaped configuration in its second state 1000B upon insertion of the second mating member 200 into the first mating member 100. The oval shaped coupling member 1600, is capable of returning to the first state 1000A defined by the oval configuration to couple the second mating member.

In some embodiments, the oval shaped coupling member 1600 is comprised of a flexible material and, as such, the oval shaped coupling member 1600 is elastically deformable to move between the first state 1000A and second state 1000B. The oval shaped coupling member 1600 may deflect radially outwards R into its round configuration 1000B upon insertion of the second mating member 200. The oval shaped coupling member 1600, moves outward to allow a raised portion of the second mating member 200, for example a bump, a lip, or a ring on the dilator hub 228, to advance into the housing 124 of the first mating member 100. The oval shaped coupling member 1600 is moveable thereafter into its first oval configuration 1000A to couple the second mating member 200 to the first mating member 100. This is illustrated in FIGS. 6B, 6C, 8B, and 8C.

In some embodiments of the each of the pair of cantilevers 1010 of the oval shaped coupling member 1600 (as shown in FIG. 6D(i), FIG. 8A) is moveable in a plane P2 that is perpendicular to the direction of advancement D of secondary mating member 200 into the housing 124 for insertion. In some such embodiments, the snap force (i.e. the force required for coupling the second mating member 200 to the first mating member 100 using the coupling mechanism 300) is independent of the proximal length of the first mating member 100. As a result, the frictional forces from insertion of the second mating member into the first mating member 100 against the coupling member 1000 can be minimized and as a result there is reduced drag. Thus, additional frictional forces are substantially not introduced and are not additive to the snap force required to deflect the coupling member 1000 to enable coupling. As such the insertion and removal forces are substantially determined by the coupling member 1000. In some embodiments of the present invention, the insertion and removal force Fi, Fr are about 15 N.

With reference now to FIG. 8F(i) and FIG. 8F(iii), the first mating member 100, for example a first mating member found on a sheath 120, has a hub 104 that further comprises a valve 150, wherein the oval shaped coupling member 1600 may be oriented in a plane P2 that is perpendicular to the direction of advancement D of the second mating member 200 (as shown in FIG. 8A). In this orientation, the oval shaped coupling member 1600 does not hinder the visibility of the valve 150 from the user. In other words, in the orientation shown, the oval shaped coupling member does not require use of the hub length L for the cantilever 1010 lengths. In some such embodiments, the coupling mechanism 300 utilizes the width of the housing 124, provided by the diameter of the housing 124. This ensures that the snap force is independent of the hub length L. Additionally, this helps optimize visibility of the valve 150 through the opening 112 for the user by allowing it to be positioned in relative proximity to the opening 112.

As previously described, the insertion and removal forces Fi, Fr are influenced by the insertion (first) and removal (second) ramps 1633A, 1633B. These ramps 1633A, 1633B may have equivalent ramp angles which, in turn, produce substantially equivalent insertion and removal forces required to compress the snaps 1630.

Conversely, the angles on the insertion and removal ramps 1633A, 1633B may be varied to define respective insertion and removal forces. In some such examples, the first and second ramps 1633A, 1633B have varying ramp angles defining varying respective insertion and removal forces. For example FIG. 8C, provides a steeper angle on the first, insertion, ramp 1633A compared to the ramp angle for the second, removal, ramp 1633B, which would increase the insertion force Fi in comparison to the removal force. Thus, altering the insertion and removal ramp angles provides a mechanism to tune the insertion and removal forces Fi, Fr. In order to ensure the ramp angles are aligned within the housing correctly, the oval shaped coupling member 1600, may employ one or more orientation keys 1480 provide a means for orienting the oval shaped coupling member 1600 in the desired orientation. This may facilitate assembly where the removal ramp angle may be different than the insertion ramp angle.

In some embodiments of the present invention, as shown in FIGS. 8D(ii), 8E(ii) and 8E(iii), the snap force, defined by the insertion force Fi and the removal force Fr, can be changed by varying the wall thickness T and the snap height. In some such examples, the snap overlap X is defined as the overlap between the snap 1630 and the portion of the second mating member 200 that is inserted into the first mating member 100. For example, in a dilator 220, this portion may comprise the ridge, bump, or lip 228, as well as the portion of dilator 220 defining the groove 226 (as shown in FIG. 8F(ii)). In one such example, the wall thickness T is about 0.75 mm and the snap overlap X is about 0.5 mm. In another example, the wall thickness T is about 1.0 mm and the snap overlap is about 1.0 mm.

The oval shaped coupling member 1600 may be comprised of an elastic material, thus it remains in the elastic region upon deformation (i.e., as it flexes between the first state 1000A and the second state 1000B). In some such embodiments of the present invention, the ability of the oval shaped coupling member 1600 to remain in the elastic region during deformation and flexion, facilitates having an insertion force Fi and removal force Fr that are substantially uniform and remain substantially unchanged over multiple uses. In some examples, the oval shaped coupling member 1600 can flex since it is free floating within the housing 124. This allows the sheath hub length L to be minimized since the flexing is in a radial direction. The oval shaped coupling member 1600 may be formed integrally, or in other words having continuous geometry, which facilitates in the reduction of stress concentrations of.

In some examples, the substantially oval shaped coupling member 1600 may be composed of a resilient material such as a polycarbonate or acrylonitrile butadiene styrene (ABS). In some embodiments, the strain is substantially dependent on the structure. the strain seen by the oval shaped coupling member 1600 during flexion is less than 6% (for plastic deformation to occur, the oval shaped coupling member 1600 would require a strain of greater than about 6%). The structure of the oval shaped coupling member 1600 prevents the increase in strain by providing elastic deformation over multiple uses.

In an alternative embodiment the oval shaped coupling member 1600 is provided in a first mating member 100 of a first medical device, such as a steerable sheath 190, as shown in FIGS. 9A-9E. The oval shaped coupling member 1600 is contained or retained within the housing 124, defined by a housing base 124b and a hub cap 126. The coupling member is substantially free floating in the housing 124, where the oval shaped coupling member 1600 is configured to couple a second mating member 200 of a second medical device, such as a dilator 220, to the steerable sheath 190.

General Audible Feedback

In some embodiments of the present invention, the coupling members 1000, such as straight cantilever 1200, u-shaped 1300, and oval disc shaped 1600, are configured to generate an audible feedback upon movement between the first state 1000A and second state 1000B. With reference to FIGS. 2A(ii), 2B(ii), 3B, 3C, 4B, 4C, 5B, and 5C, the coupling members 1000 interact with the second mating member 200 upon insertion into the first mating member100. In some examples, the respective snaps 1230, 1330 and 16300 of the respective coupling members interact with a portion of the second mating member 200, such as groove 226. Once the coupling member returns from its second state 1000B to the first state 1000A, an audible click is generated, indicating insertion and coupling. Similarly, the respective snaps 1230, 1330 and 16300 of the respective coupling members interact with a portion of the second mating member 200, such as ridge or bump 228. Once the coupling member returns from its second state 1000B to the first state 1000A, upon removal of the second mating member 200 from the first mating member 100, an audible click is generated, indicating removal and decoupling.

Indicia on Hub Cap

Figure 10:
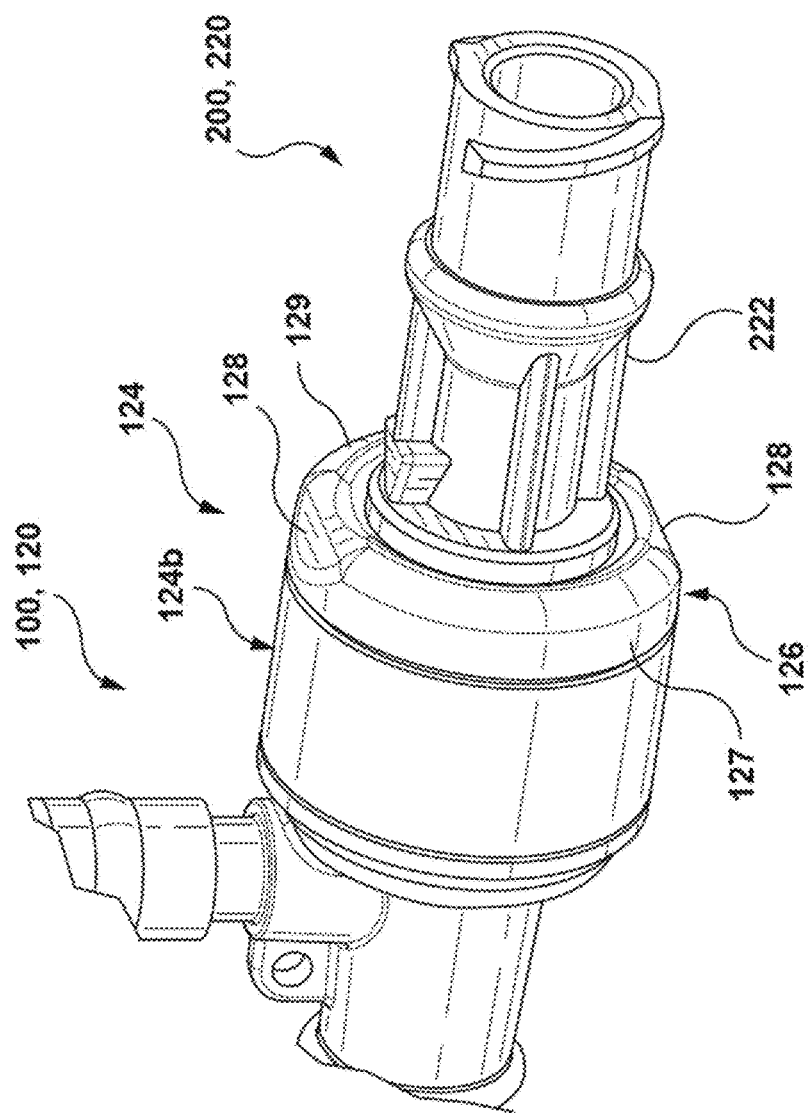
FIG. 10 is a perspective view of a first device coupled to a second device where the first device comprises a hub cap with indicia, in accordance with an embodiment of the present invention.

In some embodiments of the present invention, the hub cap 126 of the first mating member 100, for example on a sheath 120, may comprise at least one indicia 128. The indicia 128 may be positioned on the outer surface of the base portion of the housing 124b or of the hub cap 126 (as shown in FIG. 10). A visual indicia, tactile indicia, or a combination of the two may be used. Visual indicia may be comprised of a marker of a different colour, such as an arrow, a line, or a dot, to name a few. Tactile indicators may comprise an embossed or debossed portion on the hub cap 126, for example a bump, line, shape, or may comprise a beveled edge or lip. One example is illustrated in FIG. 10, where the indicia 128 comprises a pair of opposing beveled edges. The beveled edges extend from the outer surface 127 onto the proximal face 129 of the hub cap 126. Alternatively, the indicia may be a combination of the two types (i.e., both visual and tactile). For example, the indicia may comprise an embossed marker which is also denoted by a different colour.

Figure 11:
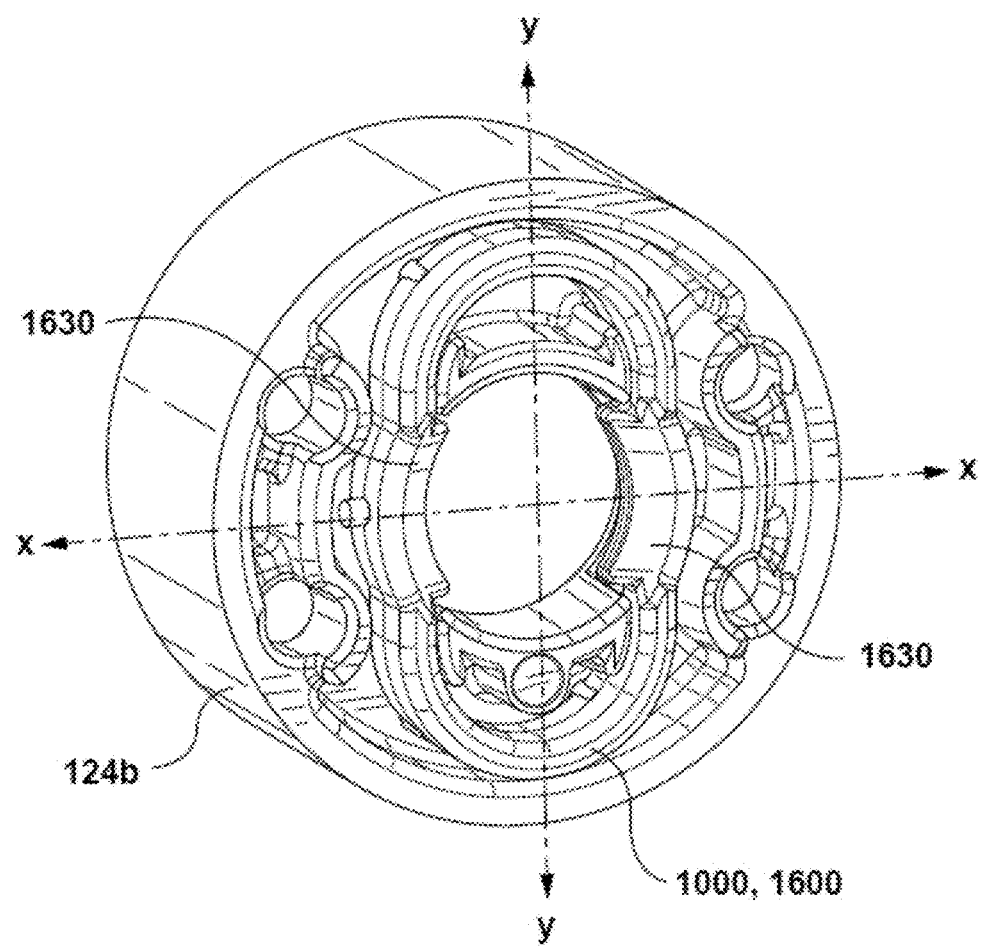
FIG. 11 is a perspective view of a coupling member of the present invention retained within a housing base portion of a first mating member.

The indicia 128 may be used to denote the orientation at which the user may grip the handle to enable a smooth uncoupling of the first mating member 100 of a first medical device from a second mating member 200 of a second medical device (i.e., uncoupling a sheath 120 and dilator 220). In an embodiment, the coupling member 1000 and the housing base 124b are functionally coupled. The hub cap 126 is positioned on top of the housing base 124b to retain the coupling member 1000 in the housing 124. FIG. 11 illustrates an example of how the housing base 124b and the coupling member 1000 are positioned relative to one another. In this embodiment, the coupling member is an oval shaped coupling member 1600.

Figure 12:
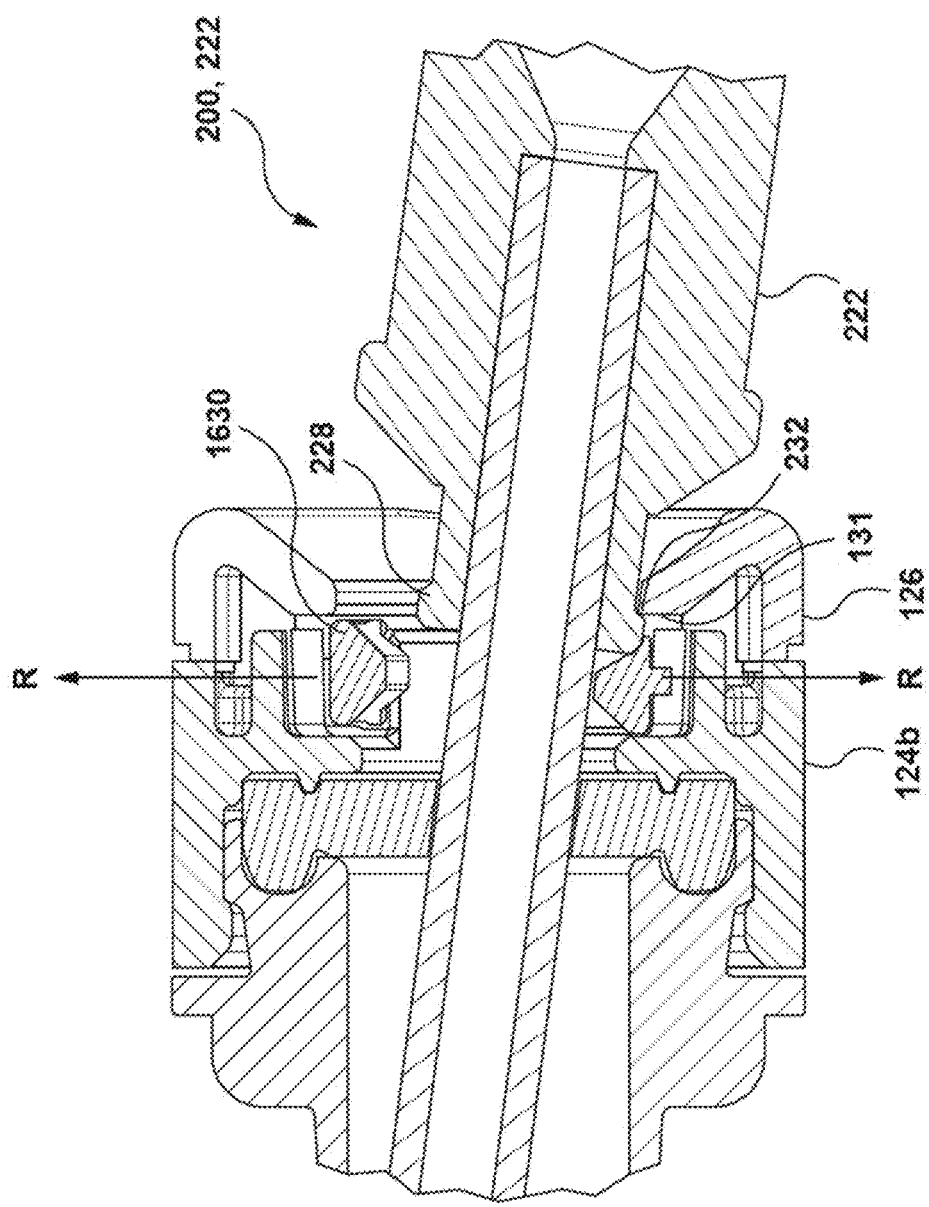
FIG. 12 is a cross sectional view of a first device and a second device illustrating the second device snagging during the removal.

During uncoupling, users may perform a "pinch and bend" technique where the dilator hub 222 (shown in FIG. 10) is pinched and bent, deflecting the snaps and thereby uncoupling the two devices (i.e., a sheath 120 and a dilator 220). With reference again to FIG. 11, ideally the dilator hub 222 is bent in the direction perpendicular (denoted by the Y arrows) to the pair of snaps 1630 of the coupling member 1000. By doing so, the bend of the dilator hub 222 will cause both snaps 1630 to deflect simultaneously. If the dilator hub 222 is bent in a different direction, for example along the line denoted by the X arrows, it may result in the dilator hub 222 snagging during uncoupling, this can be seen in FIG. 12. As the dilator hub 222 is bent into the direction of one of the snaps 1630, the snap 1630 deflects outward R. This deflection outwards R causes a space to open between the coupling member 1600 and the inner surface of the hub cap 126. The ring, lip, or bump 228 on the dilator hub 222 may then move into the space created, causing the ring, lip, or bump 228 to snag 232, for example, onto the inner edge 131 of the hub cap 126. In other words, if the dilator hub 222 is bent in a direction of a snap 1630, the oval shaped coupling member 1600 will bend disproportionately to one side (i.e., only one of the snaps 1630 will move outwards), resulting in a gap created between the snap 1630 and the inside surface of the hub cap 126; the ring, lip, or bump 228 will move into the newly created gap, catching the inside edge 131 of the hub cap 126 during uncoupling. In this situation, the catching of the ring, lip, or bump 228 may be exacerbated if the user has another device contained within the sheath 120 and dilator 220, for example a puncture device. The puncture device increases the stiffness of the system which results in the need for greater force being applied to the dilator hub 222 when the user performs the "pinch and bend" technique. This results in the snap 1630 experiencing a higher compression force, causing an increase in deflection and creating an even larger gap between the snap 1630 and the inside surface of the hub cap 126. With enough force, the ring, lip, or bump 228 can overcome the snag 232 and release which may result in a "two-step unsnap" wherein the ring, lip, or bump 228 is first released from the coupling member and then released from the snag 232. The "two-step unsnap", although feasible, is less ideal as it is unpredictable and does not provide a consistent user experience.

Figure 13A:
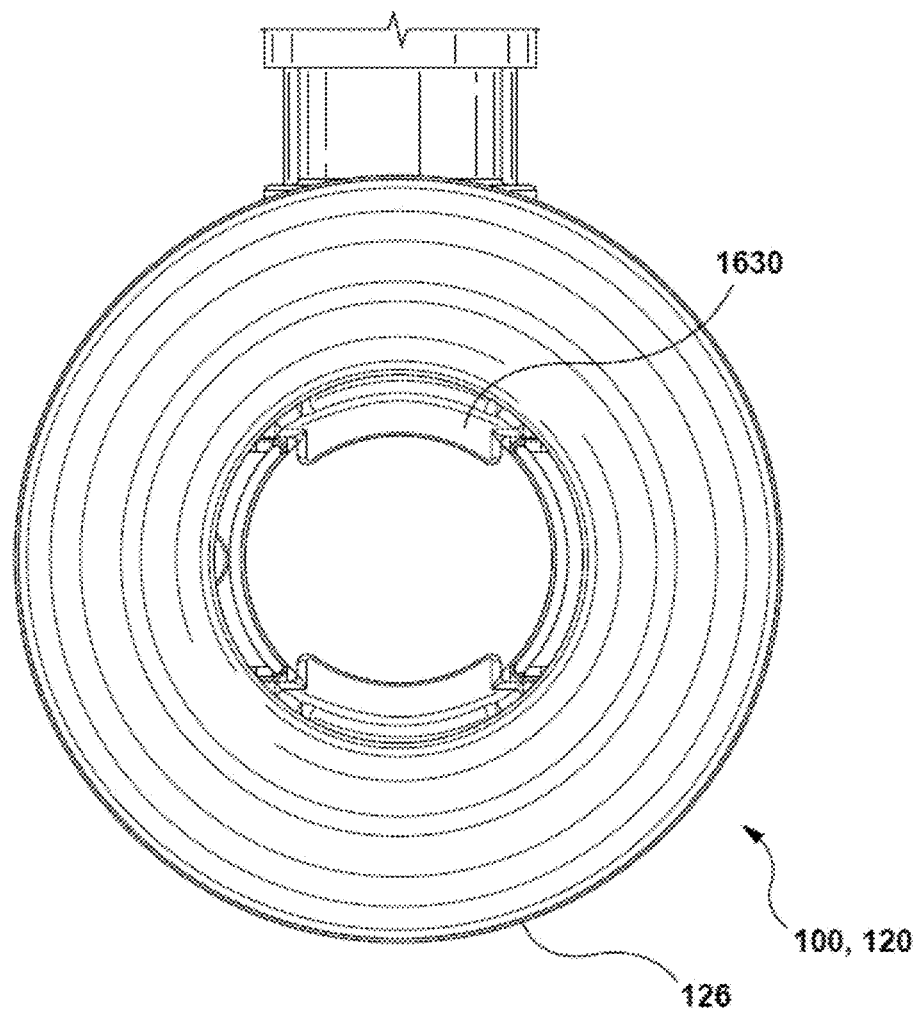
FIG. 13A is a frontal view of the first mating member hub cap where the hub cap is symmetrical, without any indicia.
Figure 13B:
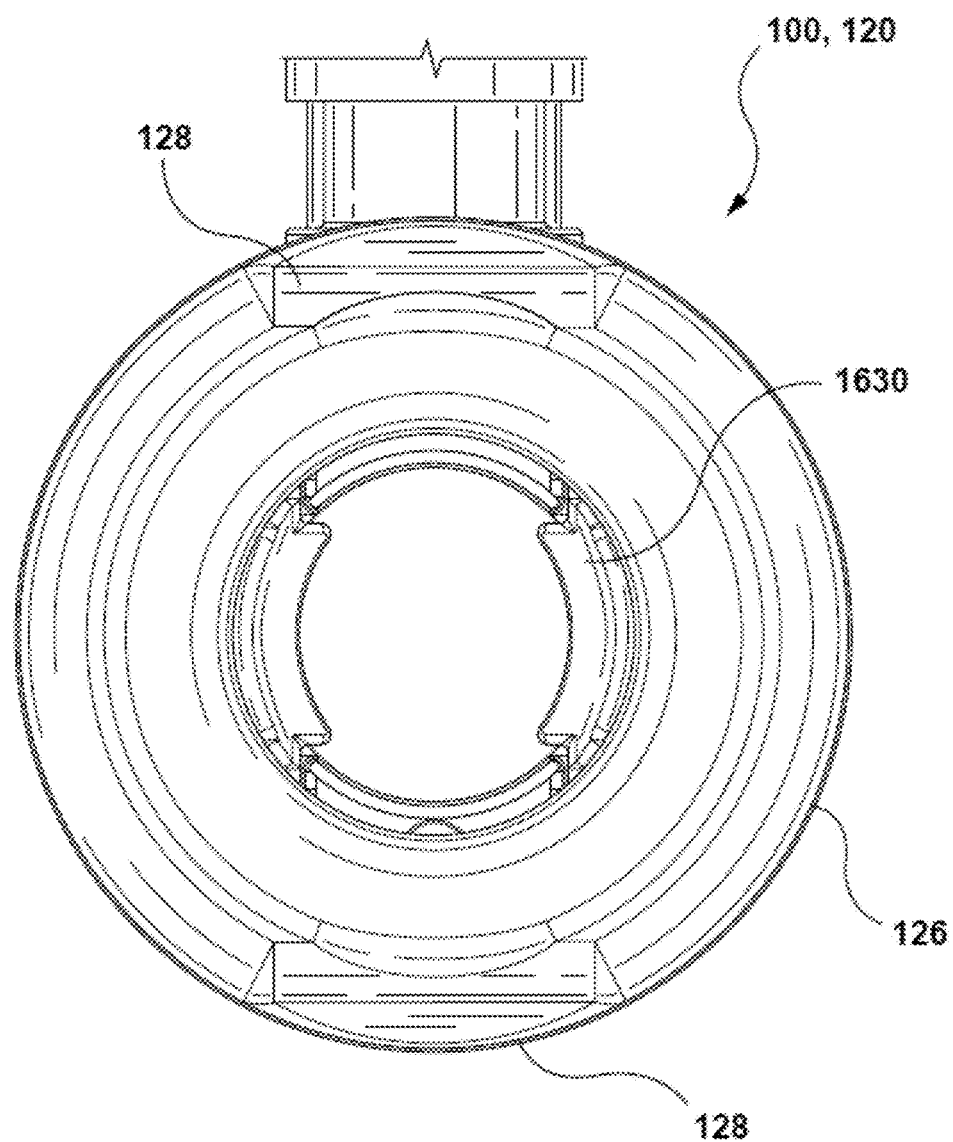
FIG. 13B is a frontal view of the first mating member hub cap where the hub cap is unsymmetrical, having indicia, in accordance with an embodiment of the present invention.

One way to provide the user with information regarding positioning of the coupling member 1000, more specifically the positioning of the snaps 1630 inside the housing 124, is to break the symmetry of the hub cap 126 (a symmetrical hub cab 126 can be seen in FIG. 13A) by positioning indicia 128 on the hub cap. During the assembly of the housing 124, the indicia 128 can be used to ensure that the hub cap 126 is oriented such that the indicia 128 is aligned in a specific way to denote the positioning of the snaps 1630, and thus, denotes the optimal bend direction to avoid the "two-step unsnap". In the embodiment illustrated in FIG. 13B, the pair of indicia 128 are positioned perpendicular to the snaps 1630, indicating to the user that they should bend the dilator hub 222 in the direction of either indicia 128 (i.e., upwards or downwards); thus, avoiding bending into a snap 1630. In an alternative embodiment, the indicia may be positioned to indicate the position of the snap 1630. In such embodiments, a user would bend the dilator hub in a direction perpendicular to the indicia.

Beveled Proximal Face of the Second Mating Member

Figure 14A:
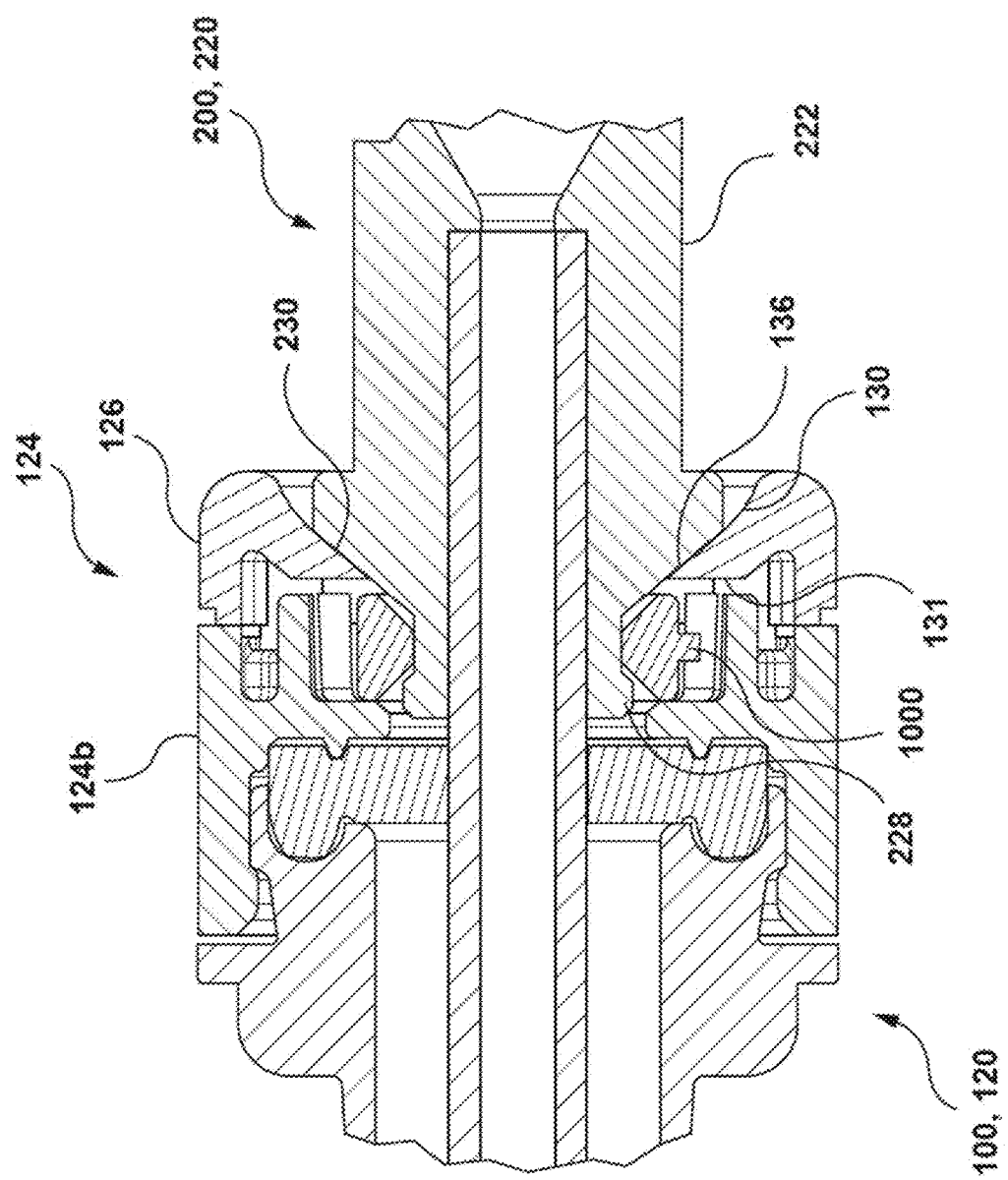
FIGS. 14A and 14B are cross sectional views of the coupled first and second mating members wherein the first mating member comprises a beveled proximal face with a sharp inner edge and a rounded inner edge, respectively.
Figure 14B:
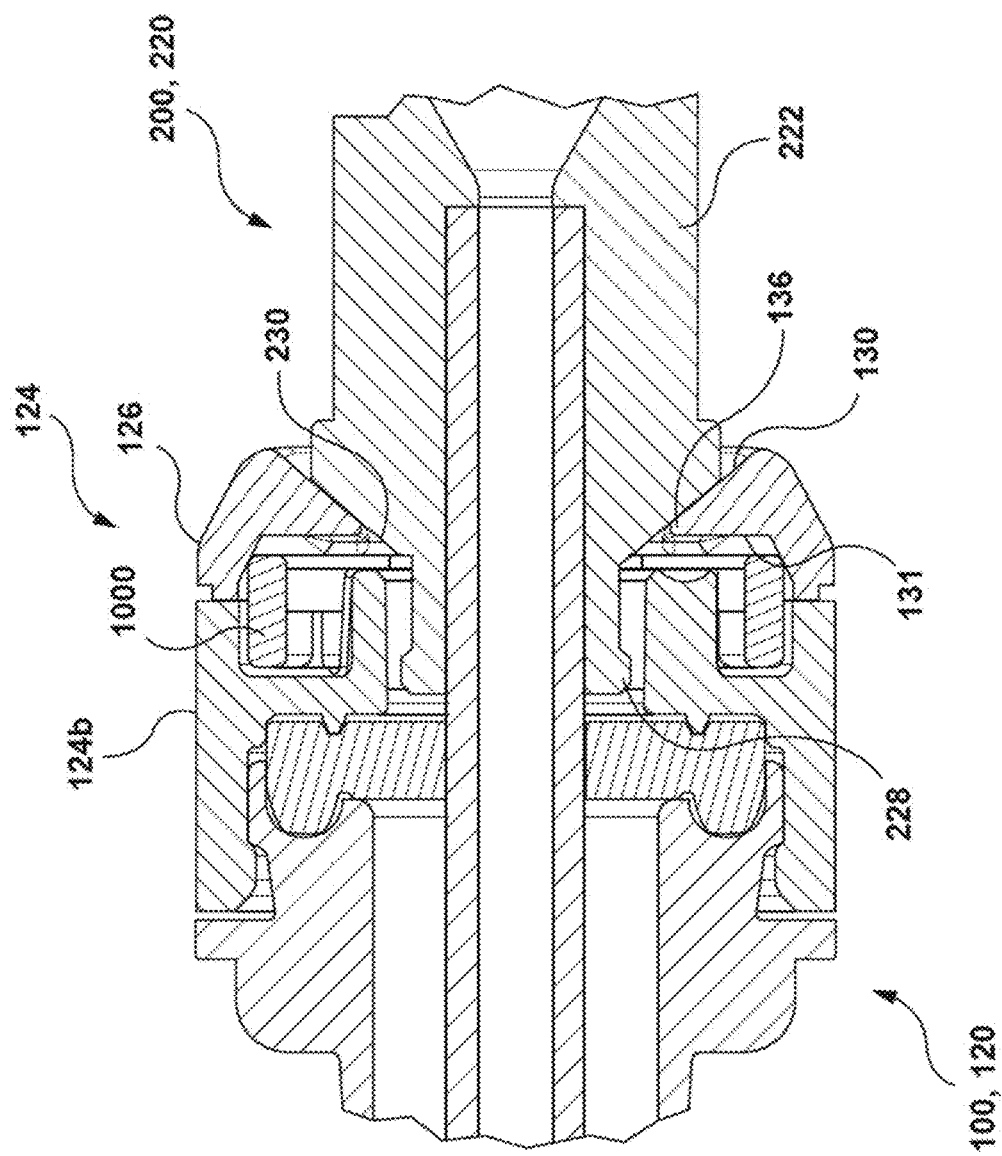

In some embodiments, the proximal face 129 of the first mating member 100 of a first medical device, such as a sheath 120, may comprise a beveled proximal face 130, as seen in FIGS. 14A and 14B. The beveled proximal face 130 facilitates a smooth uncoupling by creating a sharp edge 136 (see FIG. 14A) or rounded edge 134 (see FIG. FB), thereby creating less chance for the ring, lip, or bump 228 to snag upon removal. Additionally, the second mating member 200 of a second medical device, such as a dilator 220, may comprise a dilator hub 222 with a distal portion comprising a beveled face 230 that corresponds to and engages with the first mating member 100 beveled proximal face 130. The beveled faces 130, 230, may be used in combination with the indicator 128 to provide the user with smooth and consistent uncoupling process. Additionally, the beveled faces 130, 230, have the added benefit of facilitating the coupling of the dilator 220 into the sheath 120. The beveled face 130 of the hub cap 126 may act as a runway for the distal tip of the dilator 220 during insertion to guide the distal tip into a lumen of sheath 120. Additionally, once the dilator hub is brought in proximity to the sheath hub, the beveled face 130 of the sheath hub guides the corresponding face beveled face 230 of the dilator hub so that the respective mating members are aligned prior to coupling.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A releasable coupling mechanism, comprising:
   a dilator, the dilator having a dilator hub positioned at a proximal end of the dilator;
   the dilator hub having a raised portion positioned at a distal end of the dilator hub
   a delivery catheter, the delivery catheter having a delivery catheter hub positioned at a proximal end of the delivery catheter;
   the delivery catheter hub defining a housing;
   a coupling member completely enclosed within the housing of the delivery catheter hub, the coupling member having a pair of inwardly protruding engagement members positioned on opposing sides of the coupling member, wherein the inwardly protruding engagement members are configured to releasably engage the raised portion of the dilator hub; and,
   at least one indicia located on the housing of the delivery catheter hub, wherein the at least one indicia indicates an orientation of the delivery catheter hub such that the dilator hub disengages from the coupling member by simultaneously deflecting the pair of engagement members.

2. The releasable coupling mechanism of claim 1, wherein the at least one indicia comprises a tactile indicia, a visual indicia, or a combination of tactile and visual indicia.

3. The releasable coupling mechanism of claim 2, wherein the combination of tactile and visual indicia is at least one beveled edge.

4. The releasable coupling mechanism of claim 1, wherein the coupling member is oval, and the pair of engagement members extend inwardly towards a center of the oval.

5. The releasable coupling mechanism of claim 4, wherein the pair of engagement members deflect in a radial direction.

6. The releasable coupling mechanism of claim 1, wherein the pair of engagement members are configured to deflect from a first state to a second state upon insertion of the dilator hub, wherein the distance between the pair of engagement members in the first state is less than the distance between the engagement members in the second state has been amended to recite a distance between the pair of engagement members in the second state.

7. The releasable coupling mechanism of claim 6, wherein the pair of engagement members are configured to return to the first state upon removal of the dilator hub.

8. The releasable coupling mechanism of claim 6, wherein the dilator hub comprises a groove proximal to the raised portion, the groove having a diameter less than a diameter of the raised portion, wherein when the dilator hub is inserted, the raised portion deflects the pair of engagement members from the first state to the second state, and wherein when the dilator hub is inserted further the pair of engagement members return to the first state, settling into the groove whereby the pair of engagement members are retained, and whereby the delivery catheter hub and the dilator hub are coupled, enabling the delivery catheter and the dilator to be advanced together throughout a transseptal procedure.

9. The releasable coupling mechanism of claim 6, wherein the coupling member is substantially oval in the first state and wherein the coupling member is substantially circular in the second state.

10. The releasable coupling mechanism of claim 1, wherein the housing comprises a base and a cap, forming an enclosure for the coupling member.

11. The releasable coupling mechanism of claim 10, wherein the cap comprises an aperture configured to receive the dilator hub and wherein the cap further comprises a beveled face from an outer edge to the aperture.

12. The releasable coupling mechanism of claim 11, wherein the dilator hub comprises a beveled surface on a distal portion that corresponds to the beveled face whereby the beveled surface on the distal portion of the dilator hub is flushed.

13. The coupling mechanism of claim 1, wherein the at least one indicia is positioned perpendicularly offset from the pair of engagement members.

14. The coupling mechanism of claim 1, wherein the at least one indicia is positioned aligned with the pair of engagement members.

15. A delivery catheter for advancing through a patient's vasculature and delivery of medical devices, the delivery catheter comprising:
    a delivery catheter hub positioned at a proximal end of the delivery catheter, the delivery catheter hub having a coupling member completely enclosed within a housing of the delivery catheter hub;
    the coupling member comprising a pair of engagement members positioned on opposing sides of the coupling member and configured to releasably engage a raised portion of a dilator hub; and,
    at least one indicia on the housing of the delivery catheter hub, wherein the at least one indicia is located on an exterior of the housing;
    whereby the at least one indicia indicates an orientation of the delivery catheter hub such that the dilator hub disengages from the coupling member by simultaneously deflecting the pair of engagement members.

* * * * *